United States Patent
Asaad et al.

(10) Patent No.: US 12,336,833 B2
(45) Date of Patent: Jun. 24, 2025

(54) NEURAL BIOMARKERS OF PARKINSON'S DISEASE

(71) Applicant: Brown University, Providence, RI (US)

(72) Inventors: Wael Farouk Asaad, Westwood, MA (US); Minkyu Ahn, Pohang Gyeongbuk (KR); Shane Lee, Providence, RI (US); Peter Maxwell Lauro, Providence, RI (US); Umer Akbar, North Attleboro, MA (US); David D. Liu, Providence, RI (US); James Young Ho Yu, Los Angeles, CA (US); Daniel Esteban Amaya, Providence, RI (US)

(73) Assignee: Brown University, Providence, RI (US)

( * ) Notice: Subject to any disclaimer, the term of this patent is extended or adjusted under 35 U.S.C. 154(b) by 588 days.

(21) Appl. No.: 17/312,155

(22) PCT Filed: Dec. 11, 2019

(86) PCT No.: PCT/US2019/065697
§ 371 (c)(1),
(2) Date: Jun. 9, 2021

(87) PCT Pub. No.: WO2020/123629
PCT Pub. Date: Jun. 18, 2020

(65) Prior Publication Data
US 2022/0015686 A1  Jan. 20, 2022

Related U.S. Application Data

(60) Provisional application No. 62/778,125, filed on Dec. 11, 2018.

(51) Int. Cl.
*A61B 5/00* (2006.01)
*A61B 5/11* (2006.01)

(52) U.S. Cl.
CPC .......... *A61B 5/4082* (2013.01); *A61B 5/1124* (2013.01); *A61B 5/7246* (2013.01); *A61B 5/7267* (2013.01)

(58) Field of Classification Search
CPC .... A61B 5/4082; A61B 5/1124; A61B 5/4076
See application file for complete search history.

(56) References Cited

U.S. PATENT DOCUMENTS

2009/0318794 A1  12/2009  Descharms

OTHER PUBLICATIONS

D. P. Allen et al., "On the Use of Low-Cost Computer Peripherals for the Assessment of Motor Dysfunction in Parkinson's Disease—Quantification of Bradykinesia Using Target Tracking Tasks," in IEEE Transactions on Neural Systems and Rehabilitation Engineering, vol. 15, No. 2, pp. 286-294 (Year: 2007).*

(Continued)

*Primary Examiner* — Tse W Chen
*Assistant Examiner* — Michael A Catina
(74) *Attorney, Agent, or Firm* — Adler, Pollock & Sheehan P.C.

(57) ABSTRACT

A method includes engaging Parkinson's Disease (PD) subjects in a continuous motor performance task that elicits natural motor variability, quantifying natural motor variability of each PD subject with an array of motor metrics at short timescales, applying a machine-learning classification or regression algorithm to determine weights for each of these metrics to maximally differentiate each patient's motor performance from that of controls performing the same task, and combining the weights to determine a scalar metric of motor performance for each short epoch of motor behavior.

9 Claims, 29 Drawing Sheets

(56) References Cited

OTHER PUBLICATIONS

Kuhner A, et al. Correlations between Motor Symptoms across Different Motor Tasks, Quantified via Random Forest Feature Classification in Parkinson's Disease. Front Neurol. Nov. 14, 2017;8:607. doi: 10.3389/fneur.2017.00607. PMID: 29184533; PMCID: PMC5694559.

Yang K, et al. Objective and quantitative assessment of motor function in Parkinson's disease from the perspective of practical applications. Annals of Translational Medicine. Mar. 2016, 10.21037/atm.2016.03.09.

Maldonado-Naranjo A, et al. Kinematic Metrics from a Wireless Stylus Quantify Tremor and Bradykinesia in Parkinson's Disease. Parkinson's Disease. Apr. 2, 2019, vol. 2019; No. 6850478, pp. 1-9; DOI: 10.1155/2019/6850478.

International Search Report and Written Opinion: PCT/US19/65697; mailed Mar. 4, 2020; 9 pgs.

\* cited by examiner

|     | PD01 | PD02 | PD03 | PD04 | PD05 | PD06 | PD07 | PD08 | PD09 |
|-----|------|------|------|------|------|------|------|------|------|
| C13 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C12 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C11 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C10 | 1.00 / 0.96 / 0.98 | 1.00 / 0.96 / 0.98 | 1.00 / 1.00 / 0.98 | 1.00 / 0.96 / 0.98 | 0.99 / 0.96 / 0.98 | 0.99 / 0.91 / 0.98 | 1.00 / 1.00 / 0.98 | 1.00 / 0.97 / 0.98 | 0.98 / 0.84 / 1.00 |
| C09 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C08 | 1.00 / 0.96 / 0.98 | 1.00 / 0.96 / 0.98 | 1.00 / 1.00 / 0.98 | 1.00 / 0.96 / 0.98 | 0.99 / 0.96 / 0.98 | 1.00 / 0.91 / 0.98 | 1.00 / 1.00 / 0.98 | 1.00 / 0.97 / 0.98 | 0.99 / 0.84 / 0.98 |
| C07 | 0.98 / 0.96 / 0.89 | 0.98 / 0.96 / 0.89 | 1.00 / 1.00 / 0.89 | 0.98 / 0.96 / 0.89 | 0.98 / 0.96 / 0.89 | 0.96 / 0.91 / 0.89 | 1.00 / 1.00 / 0.89 | 0.99 / 0.97 / 0.89 | 0.93 / 0.84 / 0.89 |
| C06 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C05 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C04 | 1.00 / 0.96 / 0.99 | 1.00 / 0.96 / 0.99 | 1.00 / 1.00 / 0.99 | 1.00 / 0.96 / 0.99 | 1.00 / 0.96 / 0.99 | 0.99 / 0.91 / 0.99 | 1.00 / 1.00 / 0.99 | 1.00 / 0.97 / 0.99 | 0.99 / 0.84 / 0.99 |
| C03 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C02 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |
| C01 | 1.00 / 0.96 / 1.00 | 1.00 / 0.96 / 1.00 | 1.00 / 1.00 / 1.00 | 1.00 / 0.96 / 1.00 | 1.00 / 0.96 / 1.00 | 1.00 / 0.91 / 1.00 | 1.00 / 1.00 / 1.00 | 1.00 / 0.97 / 1.00 | 1.00 / 0.84 / 1.00 |

AUC / Sensitivity / Specificity

NEURAL BIOMARKERS OF PARKINSON'S DISEASE

CROSS REFERENCE TO RELATED APPLICATIONS

This application is a national phase filing under 35 U.S.C. § 371 of International Application No. PCT/US2019/065697 filed Dec. 11, 2019, which claims benefit from U.S. Provisional Patent Application Ser. No. 62/778,125, filed Dec. 11, 2018, the entire contents of which are hereby incorporated by reference herein.

STATEMENT AS TO SPONSORED RESEARCH

This work was supported by a Doris Duke Clinical Scientist Development Award to WFA, a Neurosurgery Research and Education Foundation (NREF) grant to WFA, the Lifespan Norman Prince Neurosciences Institute, and the Brown University Carney Institute for Neuroscience. Portions of this research were conducted using the computational resources and services at the Center for Computation and Visualization, Brown University.

BACKGROUND

The present invention relates generally to movement disorders, and particularly to the objective quantification of motor behavior as a basis to identify neurophysiological biomarkers of Parkinson's Disease (PD).

In general, a movement disorder is a neurological disturbance that involves one or more muscles or muscle groups. For example, Parkinson's disease is a progressive nervous system disorder that affects movement. Symptoms start gradually, sometimes starting with a barely noticeable tremor in just one hand. Tremors are common, but the disorder also commonly causes stiffness or slowing of movement. Although Parkinson's disease can't be cured, medications might significantly improve some symptoms.

More specifically, Parkinson's Disease (PD) is the most common neurodegenerative disease and is typified by motor and cognitive dysfunction that occur in the setting of pathologically-increased oscillatory neural activity in the basal ganglia. Oscillations in the $\beta$(~13-30 Hz) range have emerged as potential biomarkers for Parkinsonian symptoms based primarily on relatively longer timescale observations of abundant $\beta$ oscillations in the unmedicated PD state and decreased $\beta$ power in response to therapy (dopaminergic medications or DBS); critically, there are oscillations in other frequency bands that may also function as markers for effective or symptomatic motor performance, especially at shorter timescales.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In an aspect, the invention features a method including engaging Parkinson's Disease (PD) subjects in a continuous motor performance task that elicits natural motor variability, quantifying natural motor variability of each PD subject with an array of motor metrics at short timescales, applying a classification or regression algorithm to determine weights for each of these metrics to maximally differentiate each patient's motor performance from that of age-matched controls performing the same task, and combining the weights to determine a scalar metric of the quality of motor performance for each short epoch of motor behavior.

In another aspect, the invention features a method including providing a motor task to quantify rapidly fluctuating motor symptoms of Parkinson's Disease (PD) patients as a basis to identify corresponding neurophysiological biomarkers within signals recorded from the basal ganglia, including the subthalamic nucleus and globus pallidus.

In still another aspect, the invention features a method including providing a simple target-tracking task that enables a quantification of Parkinsonian motor dysfunction at short timescales using a set of metrics customized to maximally capture a patient's unique constellation of symptoms.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWING

These and other features, aspects, and advantages of the present invention will become better understood with reference to the following description, appended claims, and accompanying drawings where:

DETAILED DESCRIPTION

Figure 1:
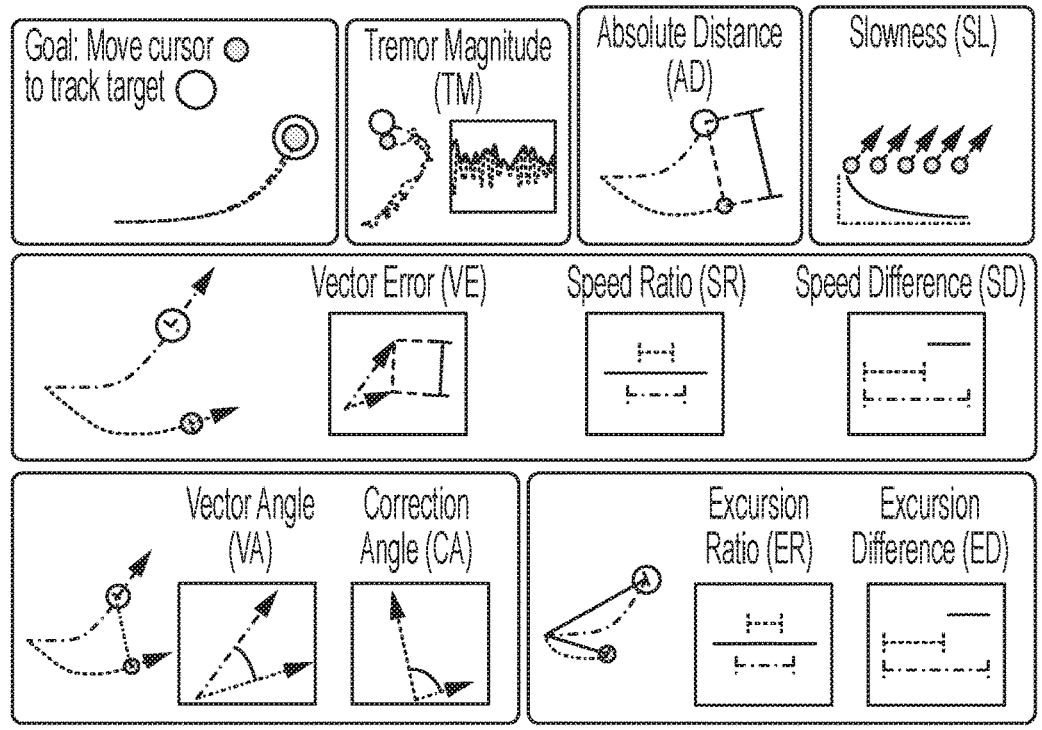
FIG. 1 illustrates exemplary object tracking task and movement metrics.
Figure 1:
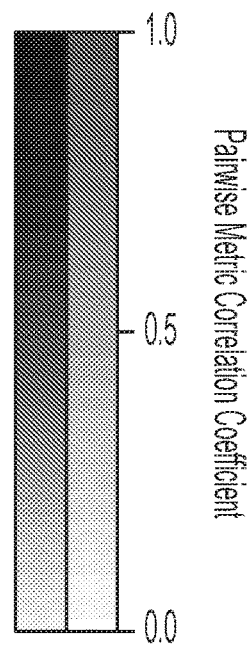

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

The following abbreviations may be found throughout the description below:

AFNI: Analysis of Functional Neuro Images (software application)
CT: Computed Tomography
DBS: Deep Brain Stimulation
MER: Microelectrode Recording
MiI: Magnetic Resonance Imaging ANN: Artificial Neural Network
PD: Parkinson's Disease
STN: Subthalamic Nucleus
SVM: Support Vector Machine Parkinson's Disease (PD) is typically characterized by a range of symptoms that may include bradykinesia, rigidity, resting tremor, and postural/gait instability, which are heterogeneously manifested across individuals. Symptom severity is typically characterized using the Unified Parkinson's Disease Rating Scale (UPDRS). Unfortunately, although validated to different extents across a number of studies, this scale ultimately relies upon subjective patient and clinician assessments and is not intended to capture fluctuations in symptoms on the timescale of seconds. Quantitative examination of PD patients' motor behavior has revealed that, within individual patients, a large dynamic range of movement speed is preserved, but shifted towards slower movements. Interestingly, faster movements that approach normal subject velocities (and that maintain normal movement accuracies) can be achieved through training, indicating the motor system retains the capability for near-normal movement in PD. Meanwhile, PD patients are notably impaired in their ability to correct for visible target deviations during ongoing movement. Based upon these observations, we observed that eliciting natural motor variability in the context of a simple visual-motor task allows the identification of neurophysiological biomarkers associated with high versus low symptom expression.

To determine which neural features co-vary with symptom expression at short timescales, the present invention is, in part, a motor task to quantify rapidly fluctuating motor symptoms as a basis to identify corresponding neural biomarkers. The present invention records neural activity from the basal ganglia, exemplified here using signals obtained from the subthalamic nucleus (STN). The magnitude of neural oscillations change in parallel with motor symptoms, even when assessing behavior and neurophysiology on short (1-10 second) timescales. Oscillations across a wide range of frequencies, including but extending well beyond β, are found to be associated with fluctuating symptom severity. Machine learning algorithms applied to these signals classify and estimate symptom severity within these short timescales. There was marked heterogeneity of oscillatory patterns across subjects such that symptom decoders generated for specific individuals failed to generalize across subjects. Our observations provide evidence that the moment-to-moment expression of motor symptoms in PD is linked to patient-specific patterns of neural oscillations may be leveraged for tracking of disease burden in a patient's natural settings using chronically-implanted devices, objective assessments of therapeutic response, and closed-loop neuromodulation.

In one aspect, the present invention is a simple visual-motor task that enables a quantification of Parkinsonian motor dysfunction at short timescales using a set of metrics that are customized to maximally capture each patient's unique constellation of symptoms. For example, some patients may be predominantly "slow and stiff" while others might be "tremor dominant", and so the ideal measures to quantify symptoms may differ across patients in this heterogenous population.

Methods of the present invention include:
(1) Engaging PD subjects in a continuous motor performance task that elicits natural motor variability and quantify these with an array of motor metrics at short (approximately 1-10 second) timescales.
(2) Applying a classification or estimation algorithm to determine weights for each of these metrics to maximally differentiate each patient's motor performance from that of age-matched controls performing the same task. In one instantiation, the applied algorithm might be support vector machine classification or regression. In other instantiations, the algorithm may employ linear discriminant analysis, neural network decoding, or other similar machine learning approaches.
(3) Using the output of the above algorithm to determine a "Symptom Score" (SS) for each short epoch of motor behavior
(4) Examining oscillatory activity in the basal ganglia, including the subthalamic nucleus (STN) or globus pallidus, while subjects performed this task to determine which neural features best reflect or predict each patient's short-timescale SS.

Quantification of Parkinsonian Motor Symptoms on Short Timescales

The tracking task required subjects to follow an on-screen target using a joystick-controlled cursor (FIG. 1A). It was designed to assess the quality of movement in a continuous fashion and at short timescales. PD patients undergoing routine, awake implantation of STN DBS electrodes (n=22) and control subjects in the clinical setting (n=15) performed this motor task. Because the heterogeneity of motor impairment in PD was unlikely be associated with some narrow aspect of performance on this task, we defined a library of 8-10 motor metrics that tiled the potential space of movement error (FIG. 1B). The precise selection of these metrics is less critical than the use of a sufficiently broad set of measures that capture motor features typical of Parkinson's Disease, such as tremor, bradykinesia, rigidity and akinesia. We calculated correlations among these metrics to assess the degree of potential redundancy (FIG. 1C) and found a wide range of correlation among individual pairs of metrics ($r^2$ ranged 0.01 to 0.67 in controls and 0.02 to 0.53 in PD subjects), but no single metric had a mean correlation ($r^2$) with all the other metrics above 0.3, consistent with the notion that the combination of these particular metrics may be mutually informative; the same would be true in other effective instantiations of this invention that use a different set of motor performance metrics.

We next combined the individual metrics into a single composite score reflecting the degree of motor impairment within a given time window. In the exemplary instantiation, a support vector machine (SVM) is applied to the metrics library to determine, for each patient, the weights on each measure that allow optimal separation between that subject's motor performance and the performance of control subjects (see FIG. 2A). Other instantiations could apply different algorithms to quantify Parkinsonian motor impairment in relation to normal motor performance.

Figure 2:
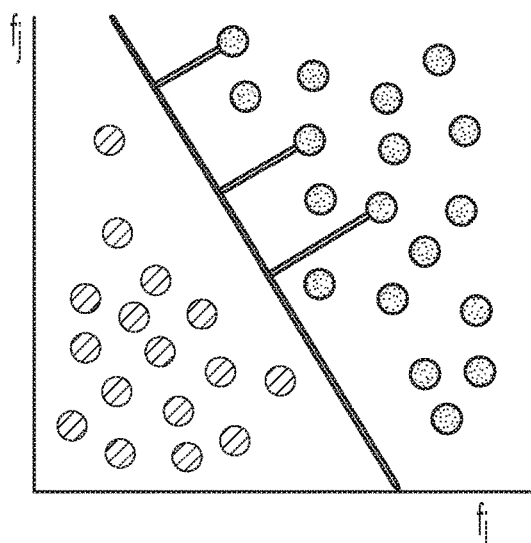
FIG. 2 illustrates exemplary SVM and symptom scores.
Figure 2:
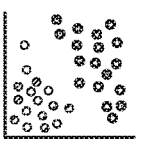
Figure 2:
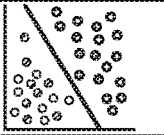
Figure 2:
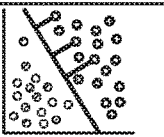
Figure 2:
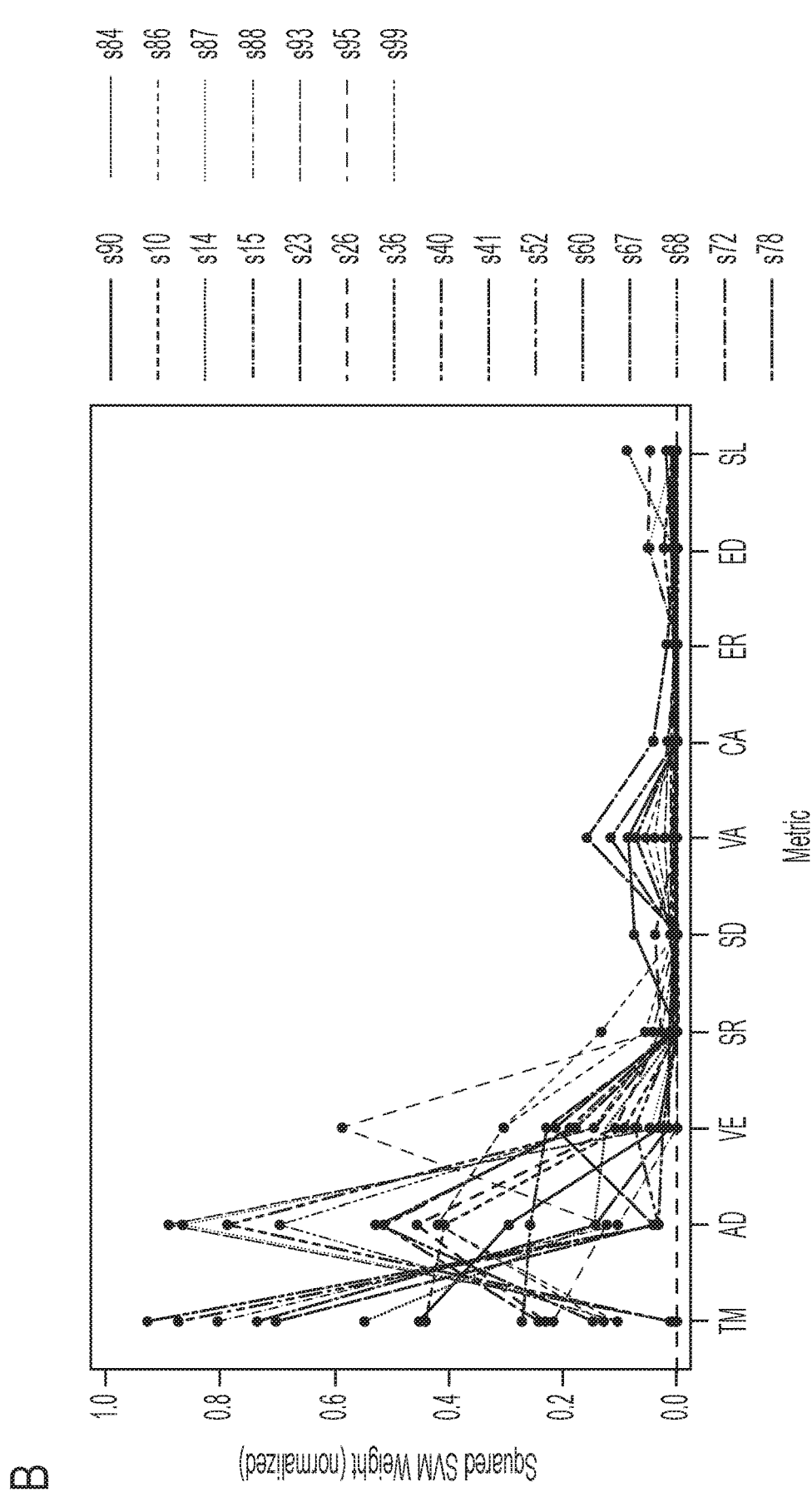
Figure 2:
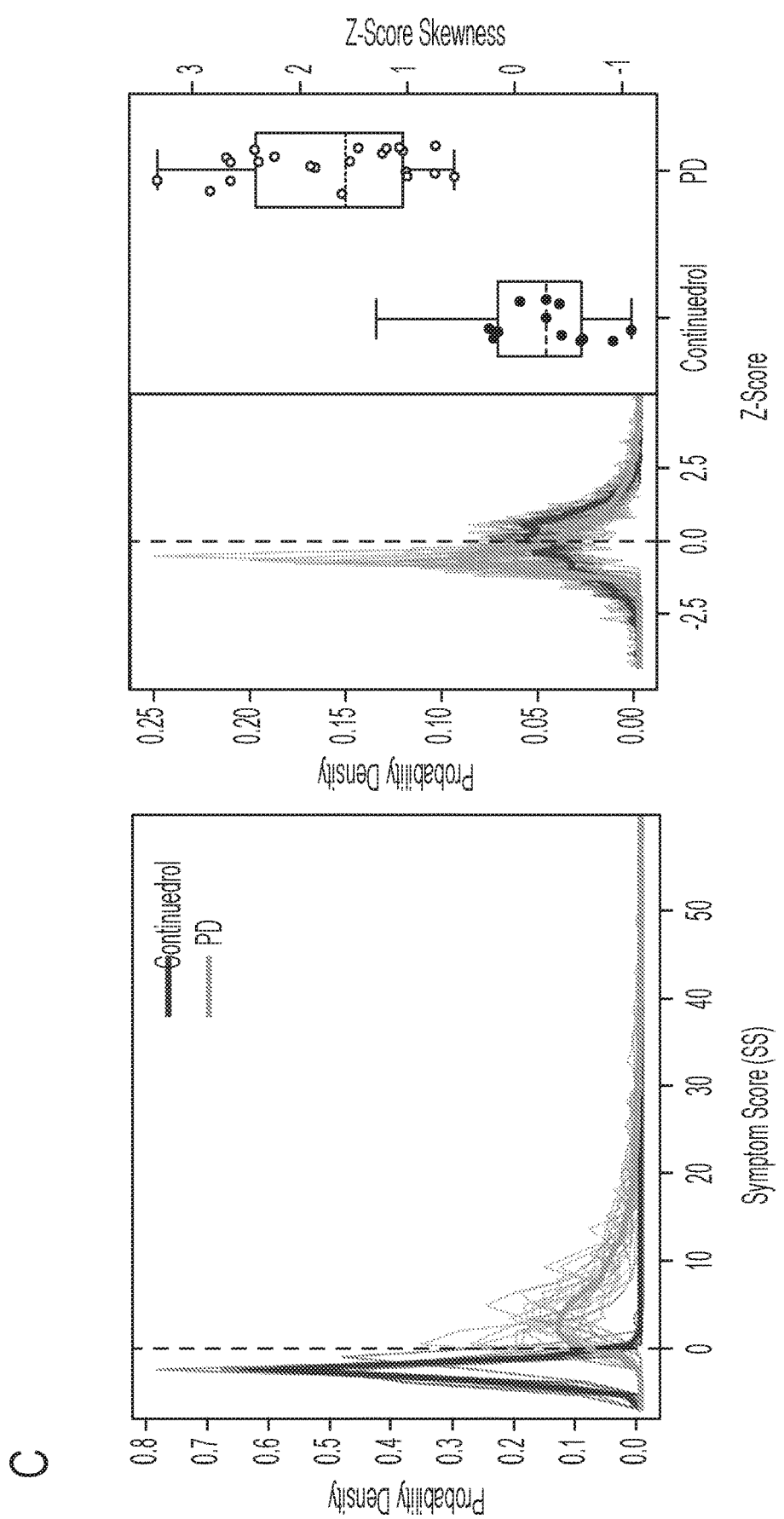
Figure 2:
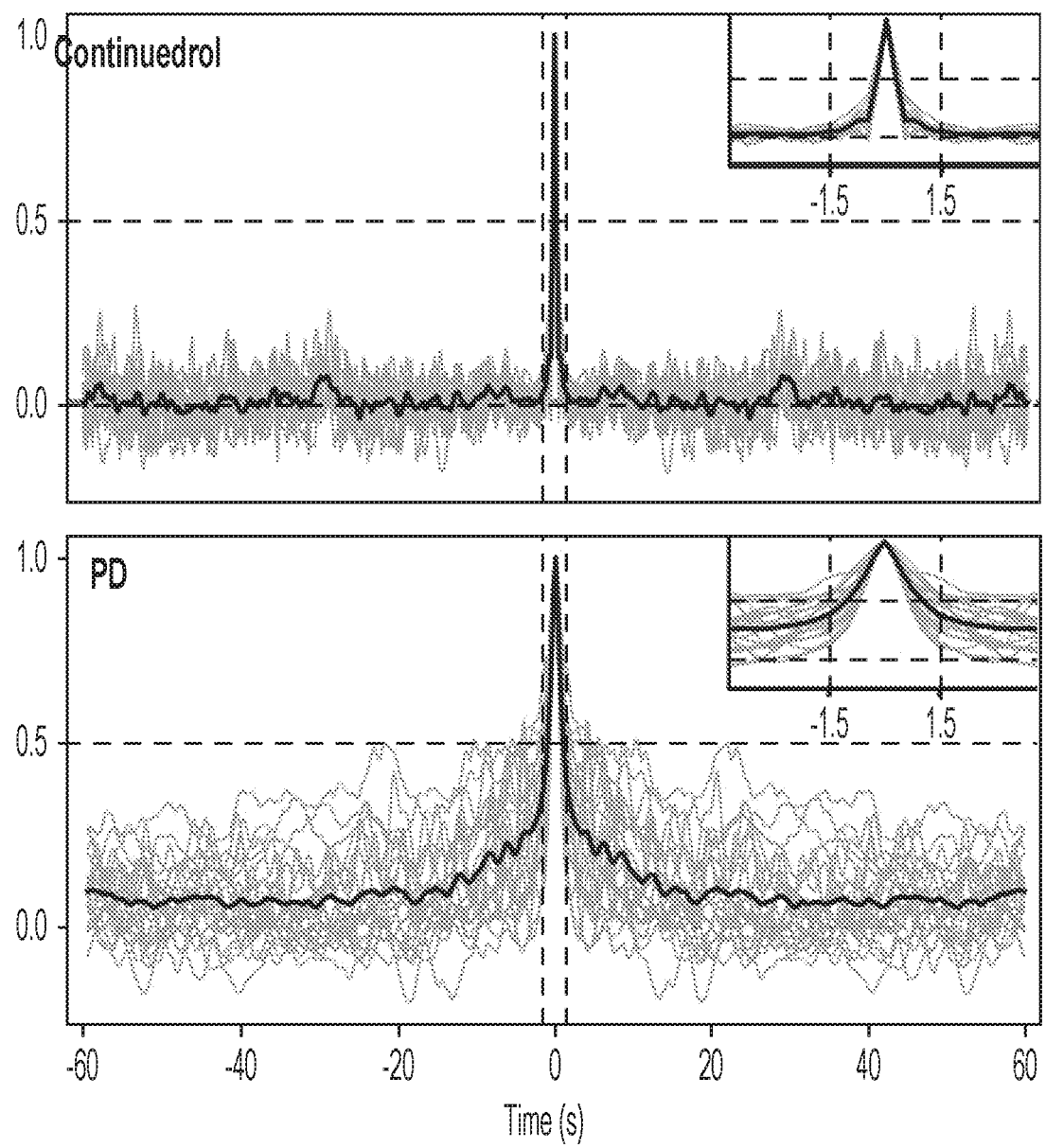
Figure 2:
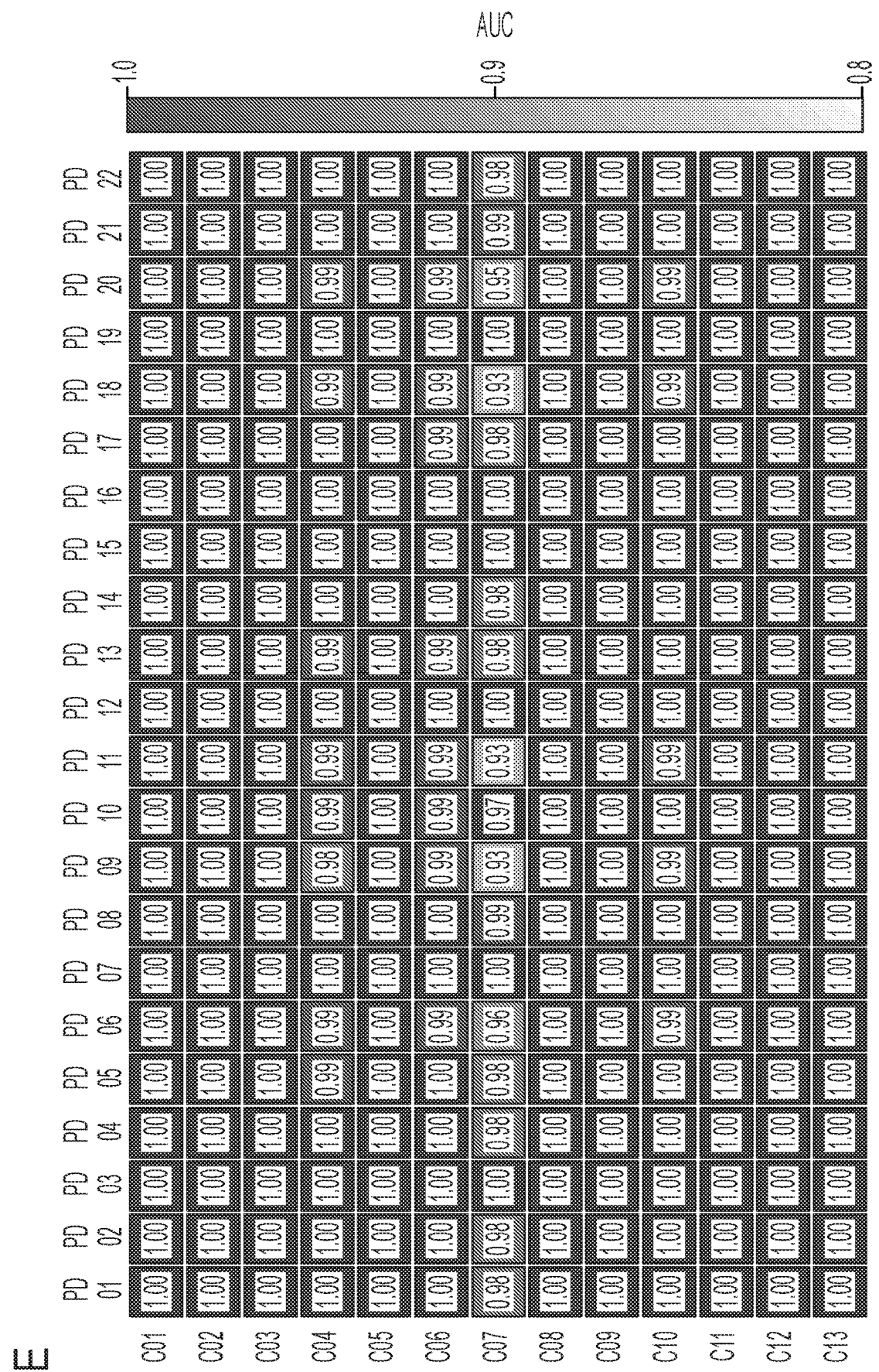

In the exemplary instantiation, motor performance was assessed in 3-second epochs and the distance between each data point and the SVM-generated hyperplane was defined as the "symptom score" (SS), though other instantiations may use somewhat shorter or longer timescales, all of which produce equivalent results. The resulting SS distributions for PD patients and controls were highly distinguishable (ROC area-under-the-curve comparing each control to each PD patient ranged: 0.93-1.00 with all p-values<0.001; FIG. 2B). The average hyperplane comparing each single patient to all controls was then used to derive the final SS values used here.

To determine the timescale of behavioral variation in each group, we examined the temporal autocorrelation of SS by shifting a copy of the time series in 500 ms steps and computing the correlation between the shifted and unshifted data. For control subjects, this revealed a narrow peak with nearly zero correlation beyond this peak, suggesting the SS for these patients were no more correlated across time than noise. In PD patients, on the other hand, a broader central peak was observed (FIG. 2D; width at half-height=±~0.25 seconds in controls and ±~1 second in PD patients) and the off-peak correlation values did not return to zero within the observed timeframe of ±1 minute, suggesting a history-dependence of successive motor states in PD that was absent in controls. The choice of a 3 second window (±1.5 seconds) for calculation of the SS was therefore roughly consistent with the observed timescale of motor fluctuation in these patients. Other instantiations of this invention may estimate the timescale of Parkinsonian fluctuation using slightly different methods (e.g., using a 3-sigma threshold), which yield somewhat different results, but all generally within 1-10 seconds, consistent with the overall approach of this invention.

Figure 3:
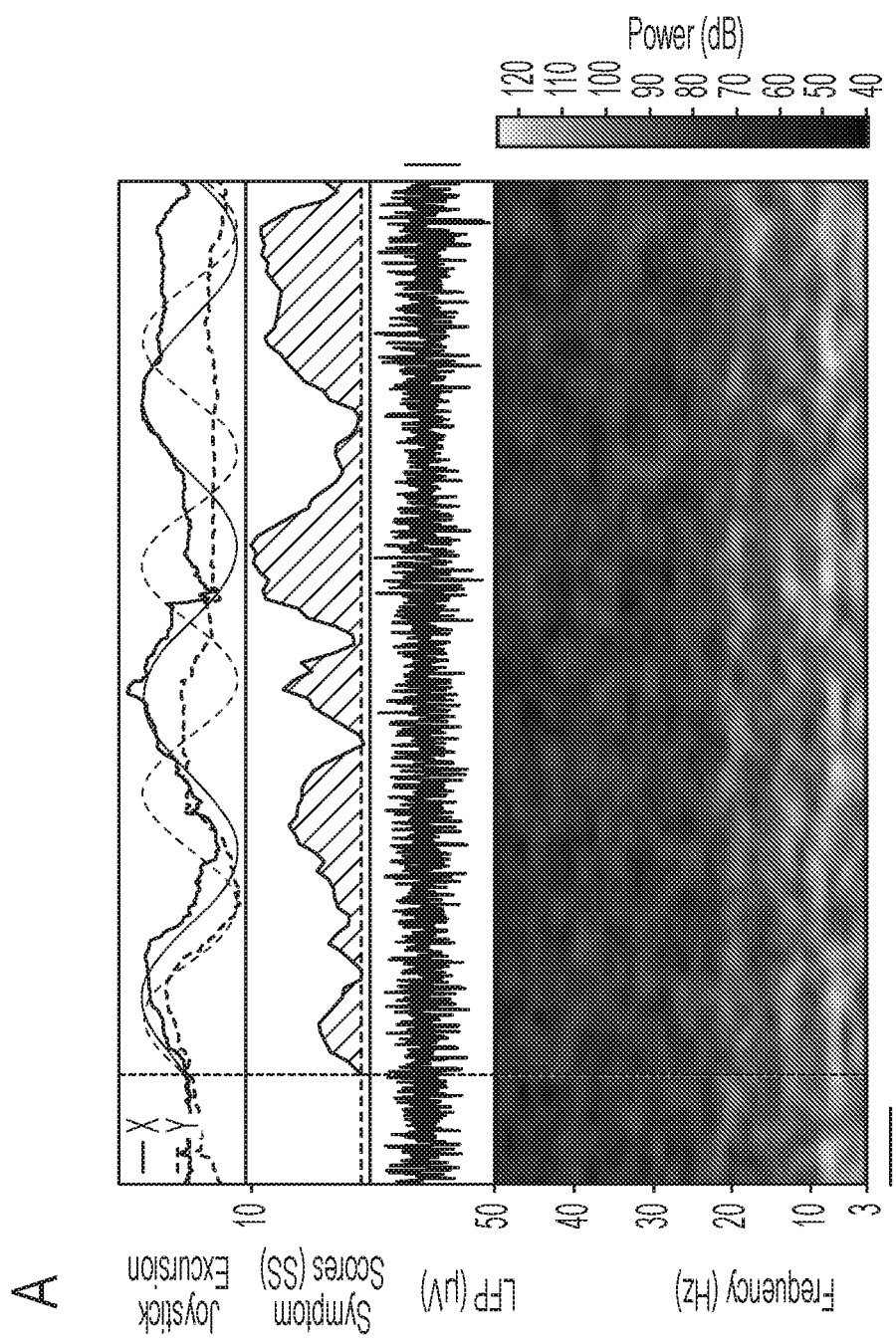
FIG. 3 illustrates exemplary intracranial recordings.
Figure 3:
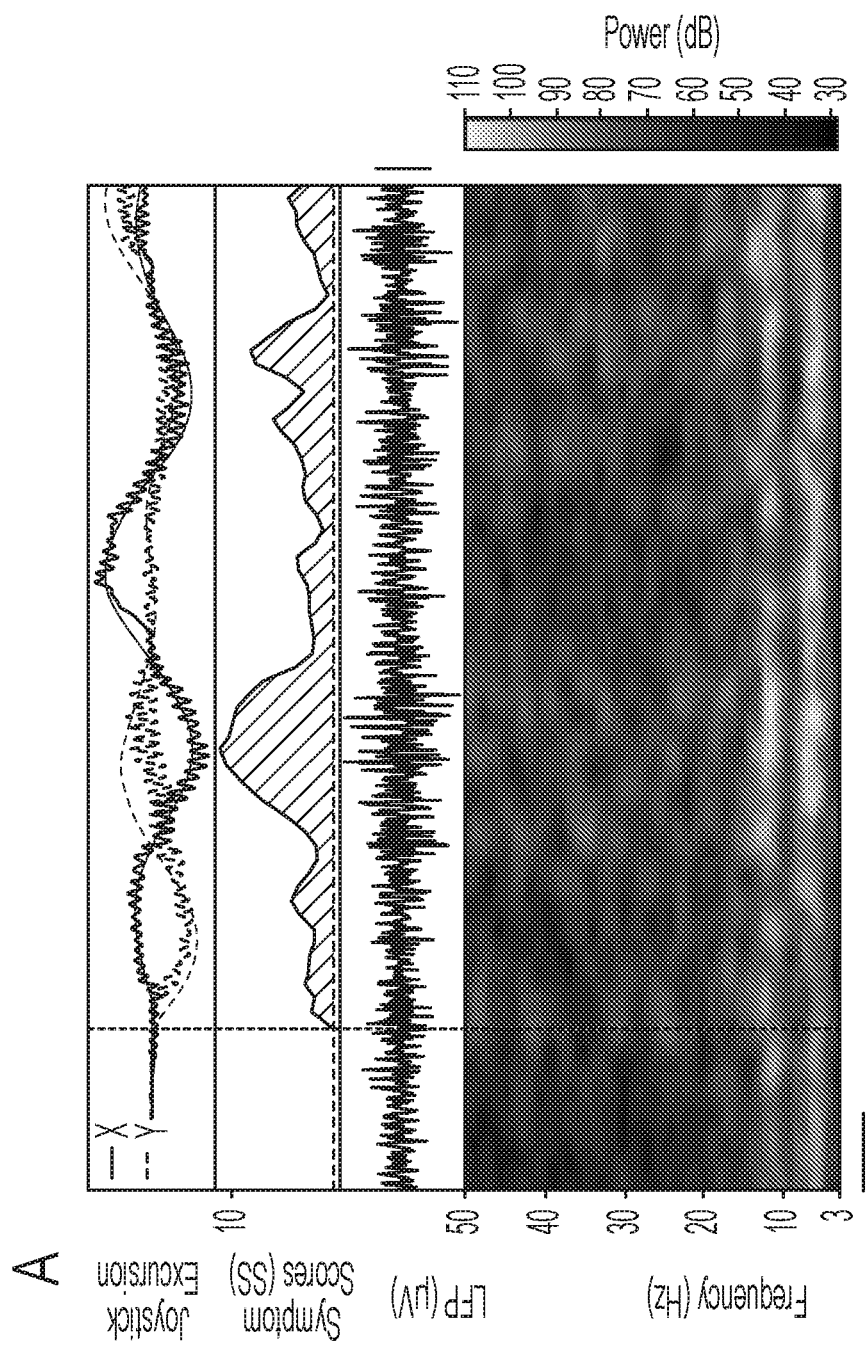
Figure 3:
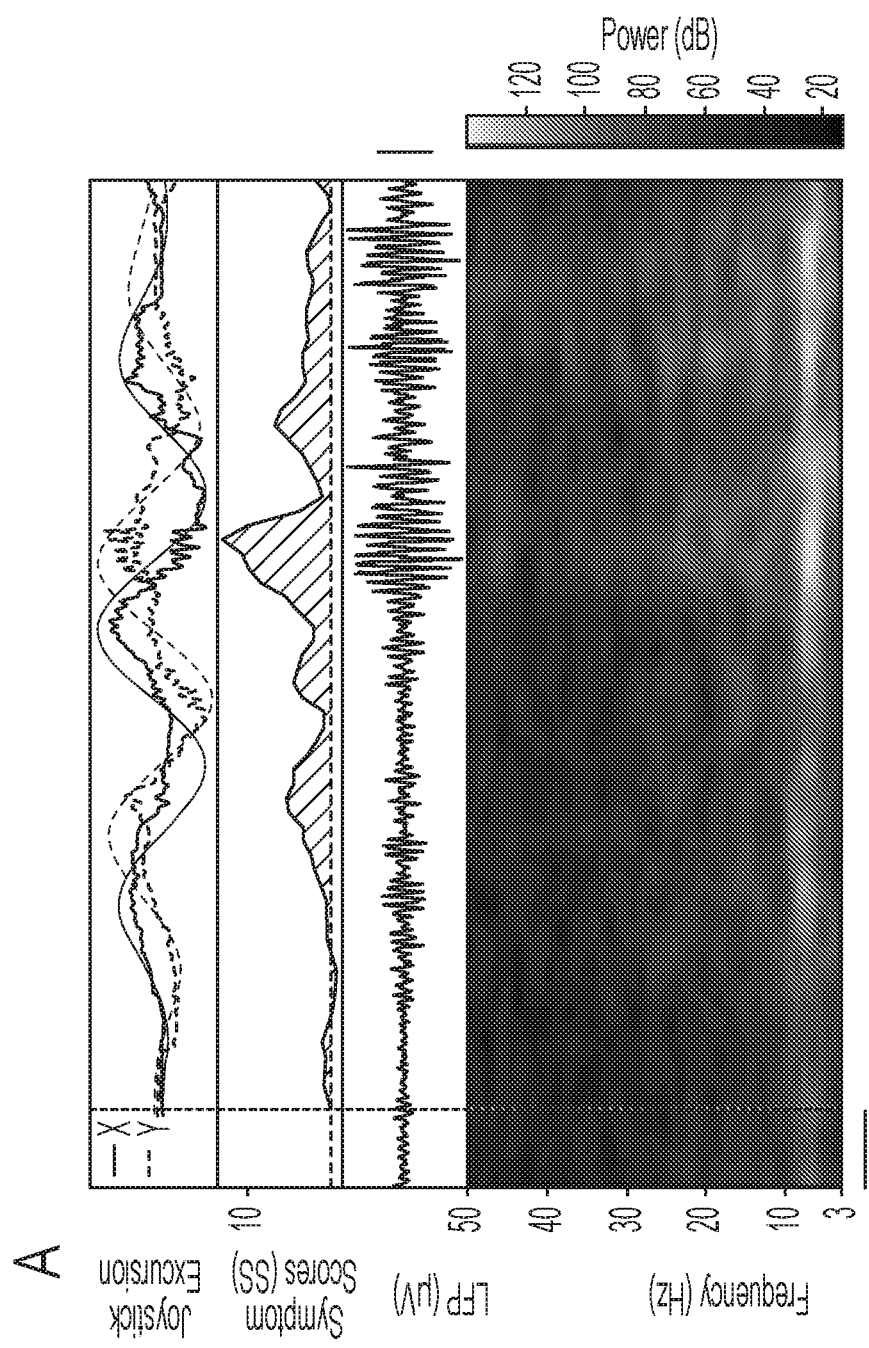
Figure 3:
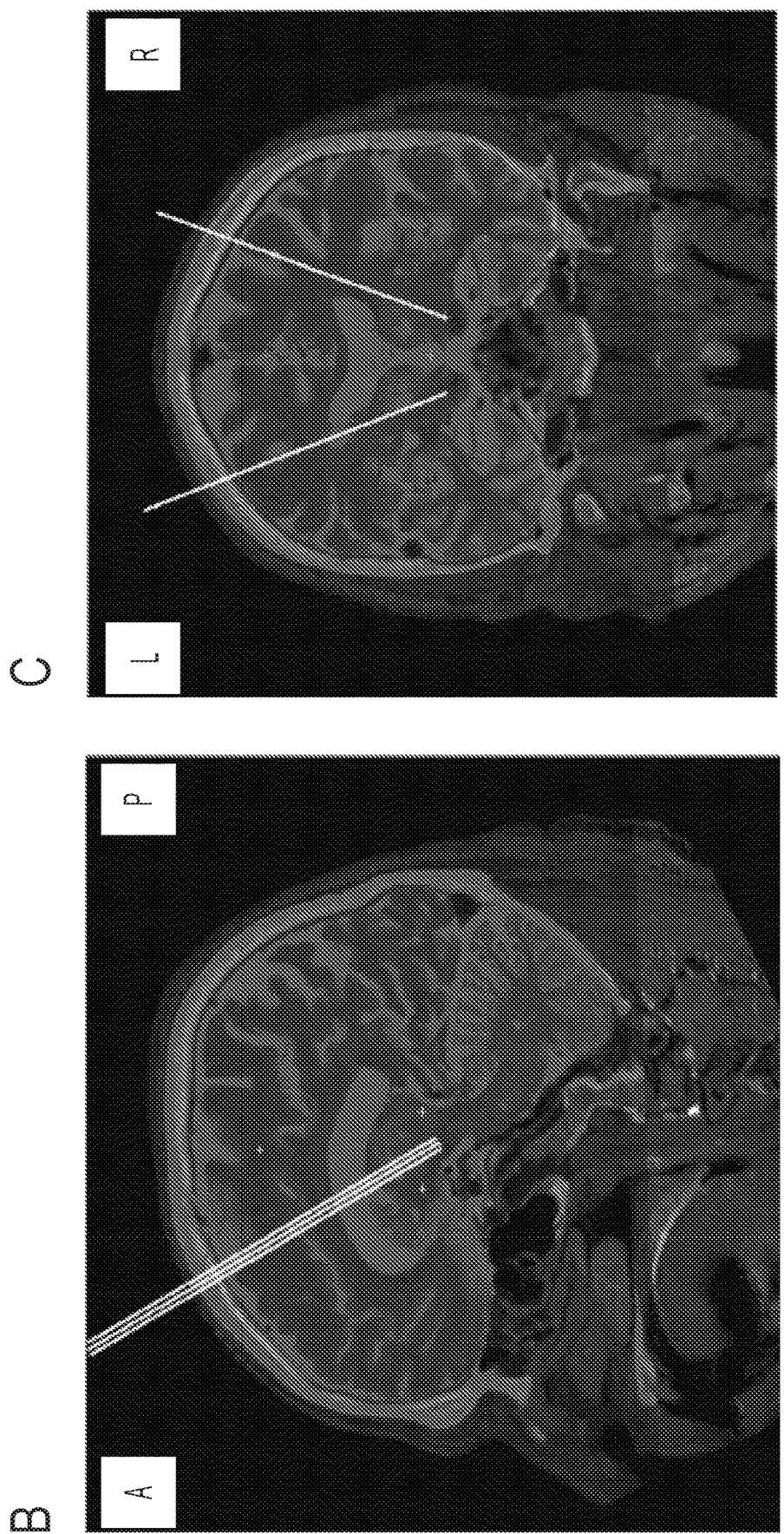
Figure 3:
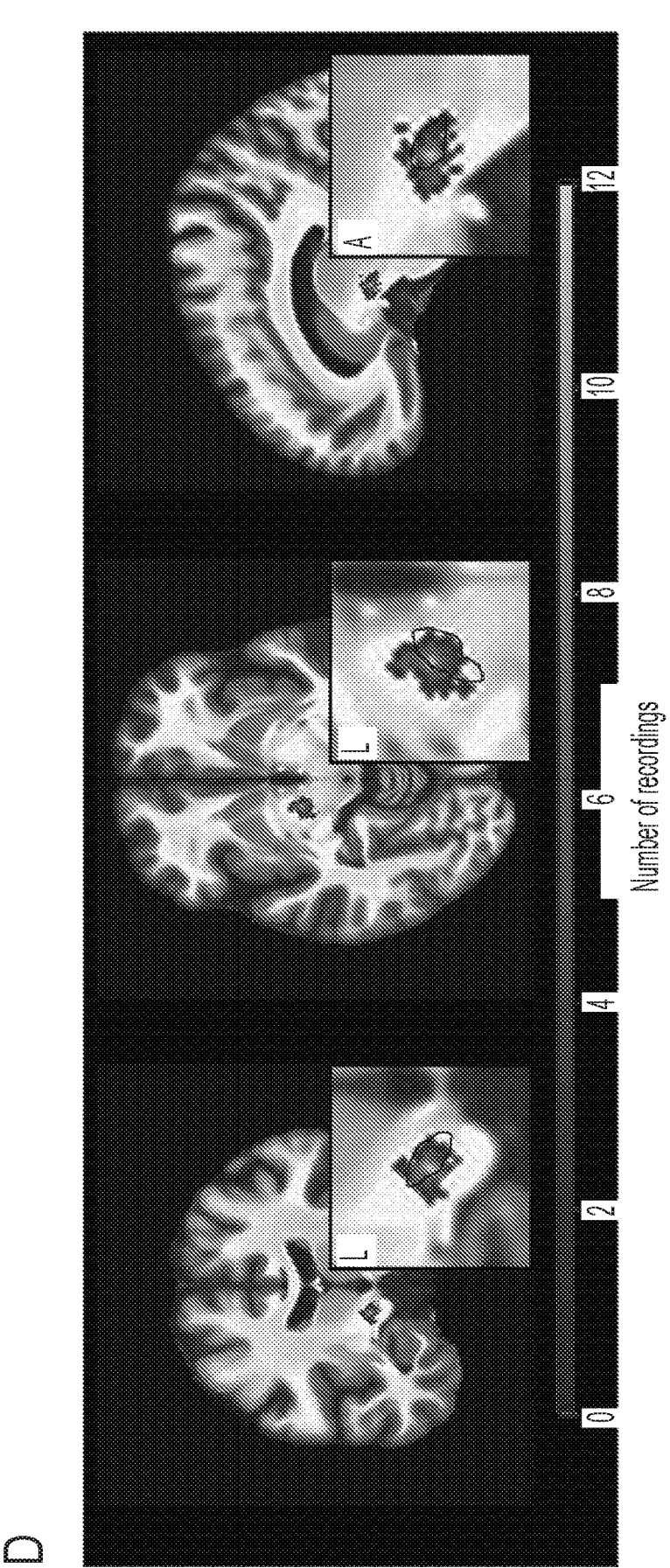

Basal Ganglia Neural Activity correlates with Symptom Severity on Short Timescales STN local field potentials (LFPs) were recorded from microelectrodes traversing the region of the STN as PD patients performed the target tracking task (FIG. 3). Patients were able to perform 1-4 sessions of the task (with recordings obtained at different depths for each session) for a total of 50 sessions. At any particular depth, data were acquired from 2-4 microelectrodes, resulting in a total of 152 recordings from the region of the STN across electrodes, sessions and patients. Neural signals from the STN contralateral to the hand used to perform the task were analyzed.

Figure 4:
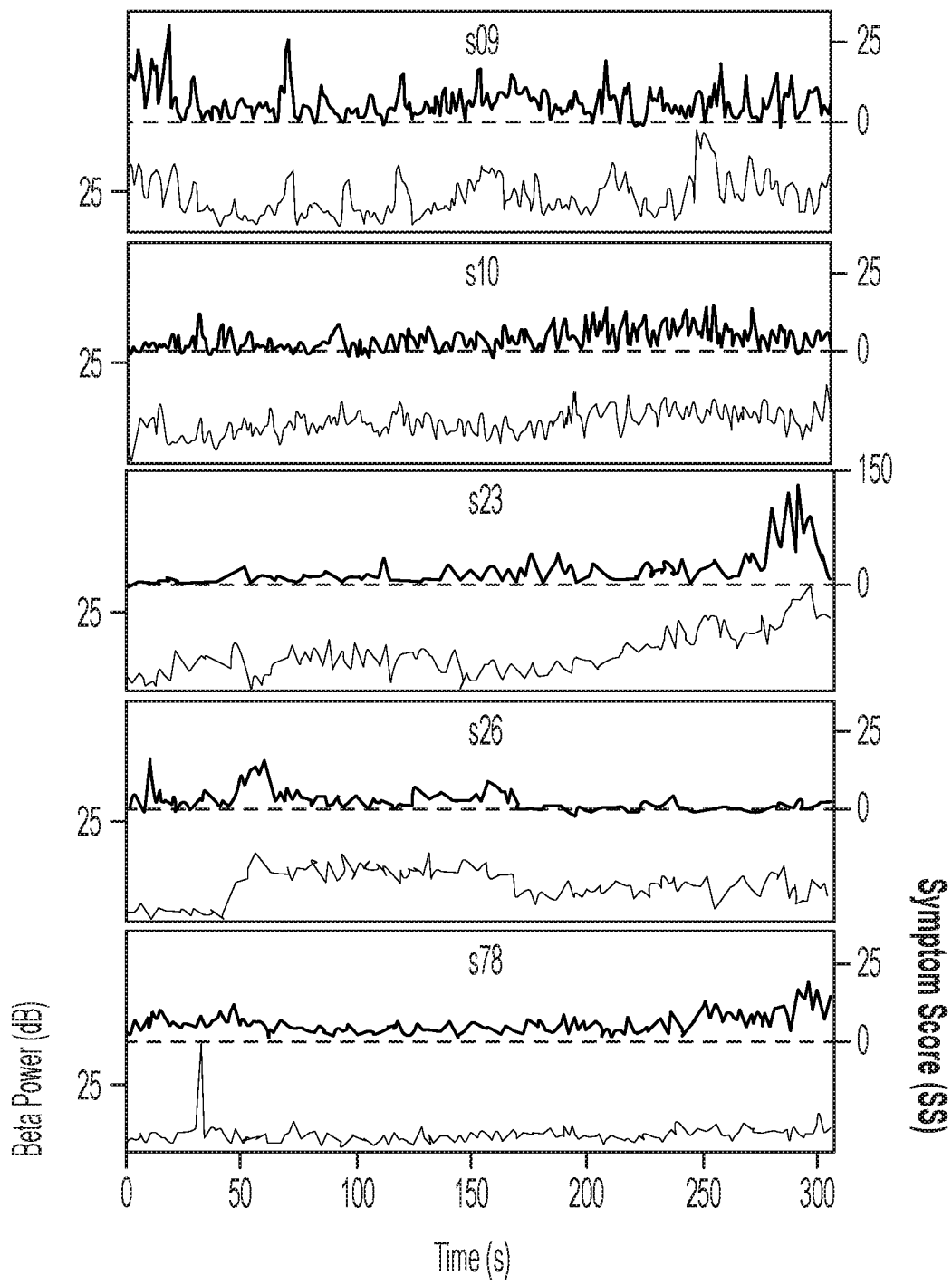
FIG. 4 illustrates exemplary broadband activity correlated with SS.
Figure 4:
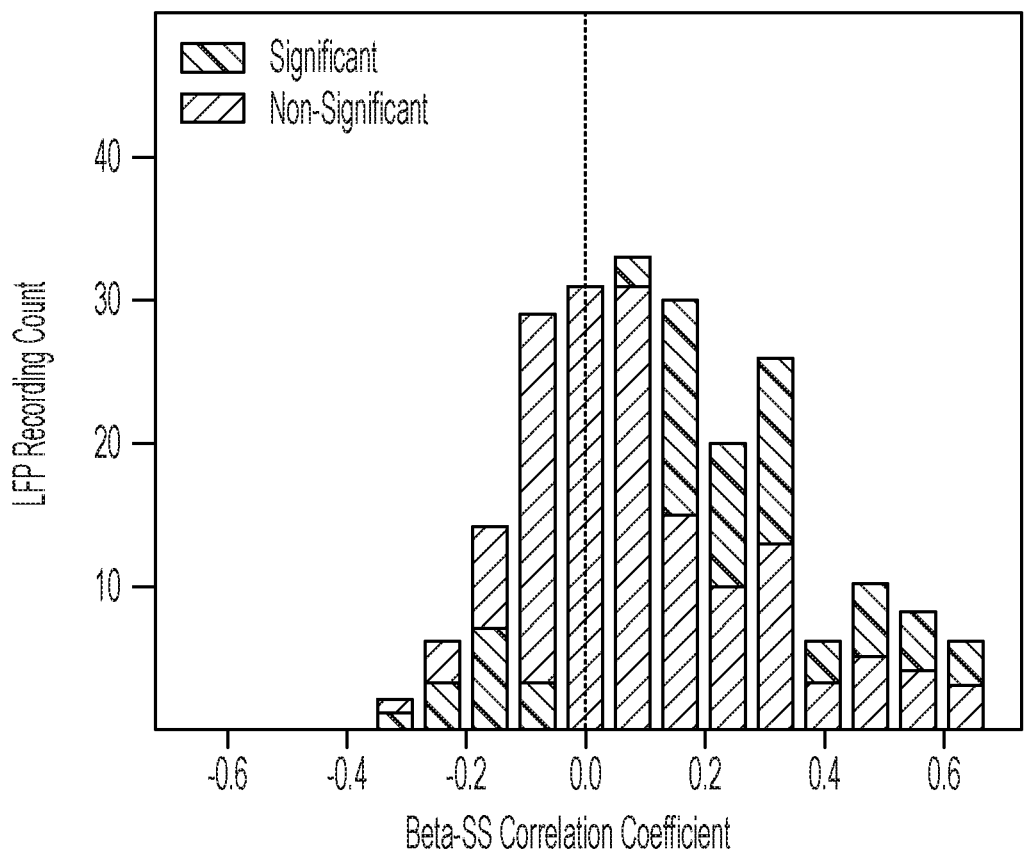
Figure 4:
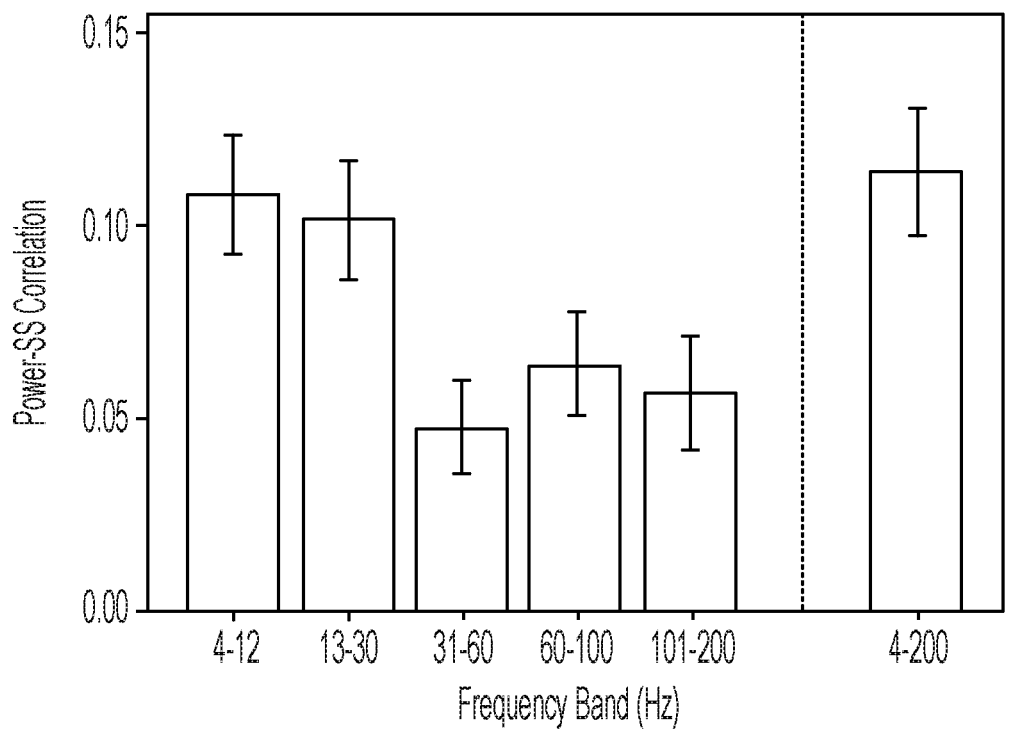
Figure 4:
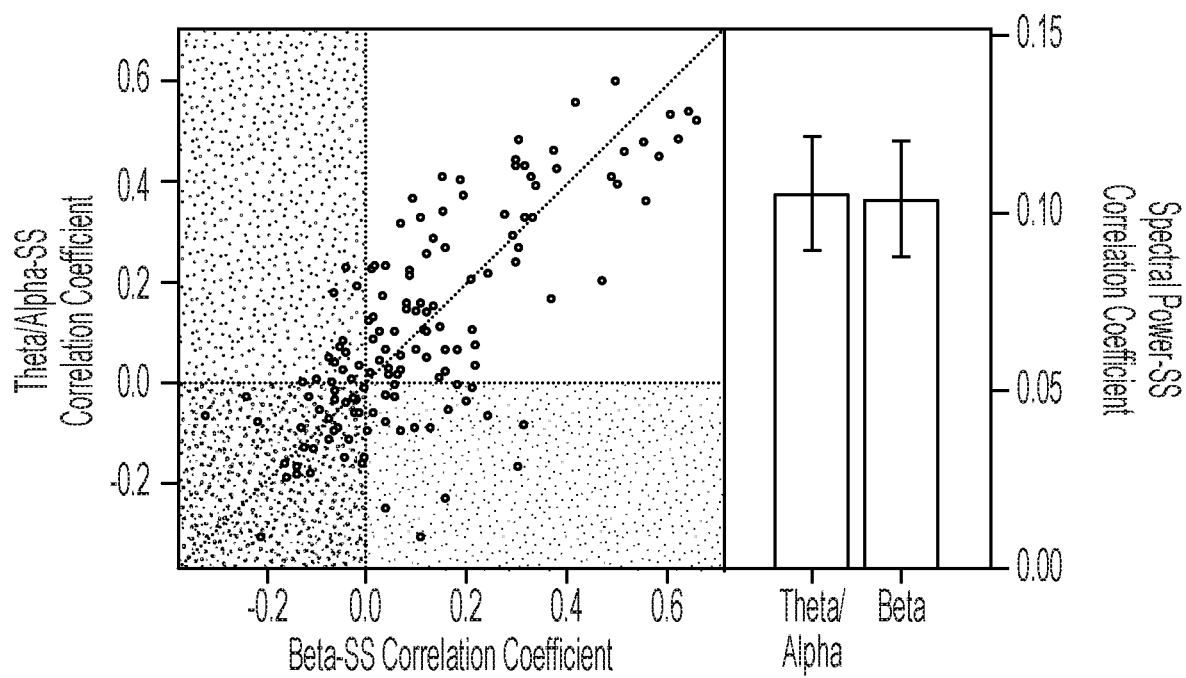
Figure 4:
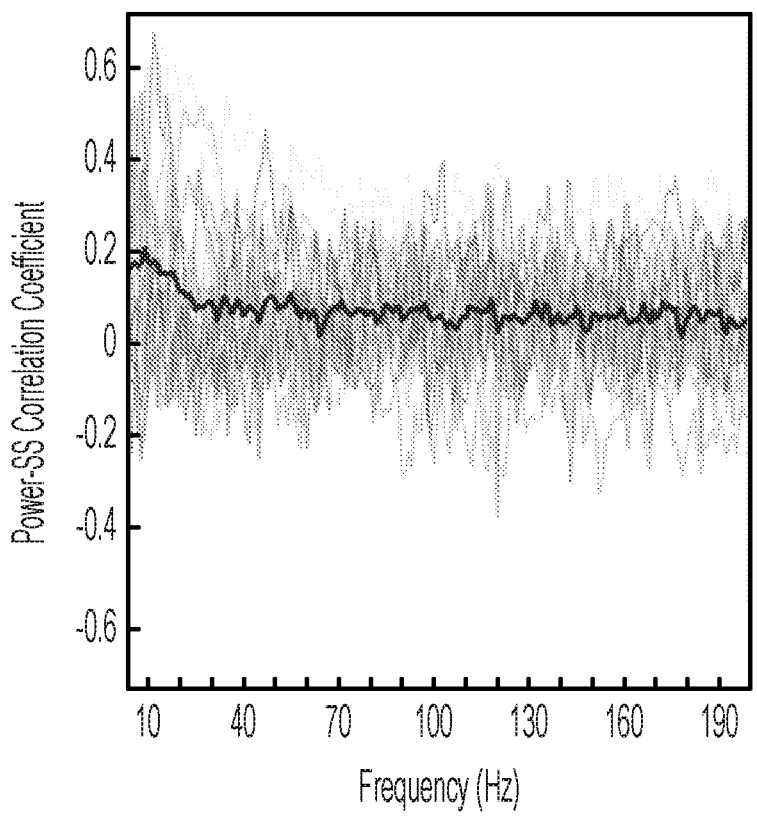
Figure 4:
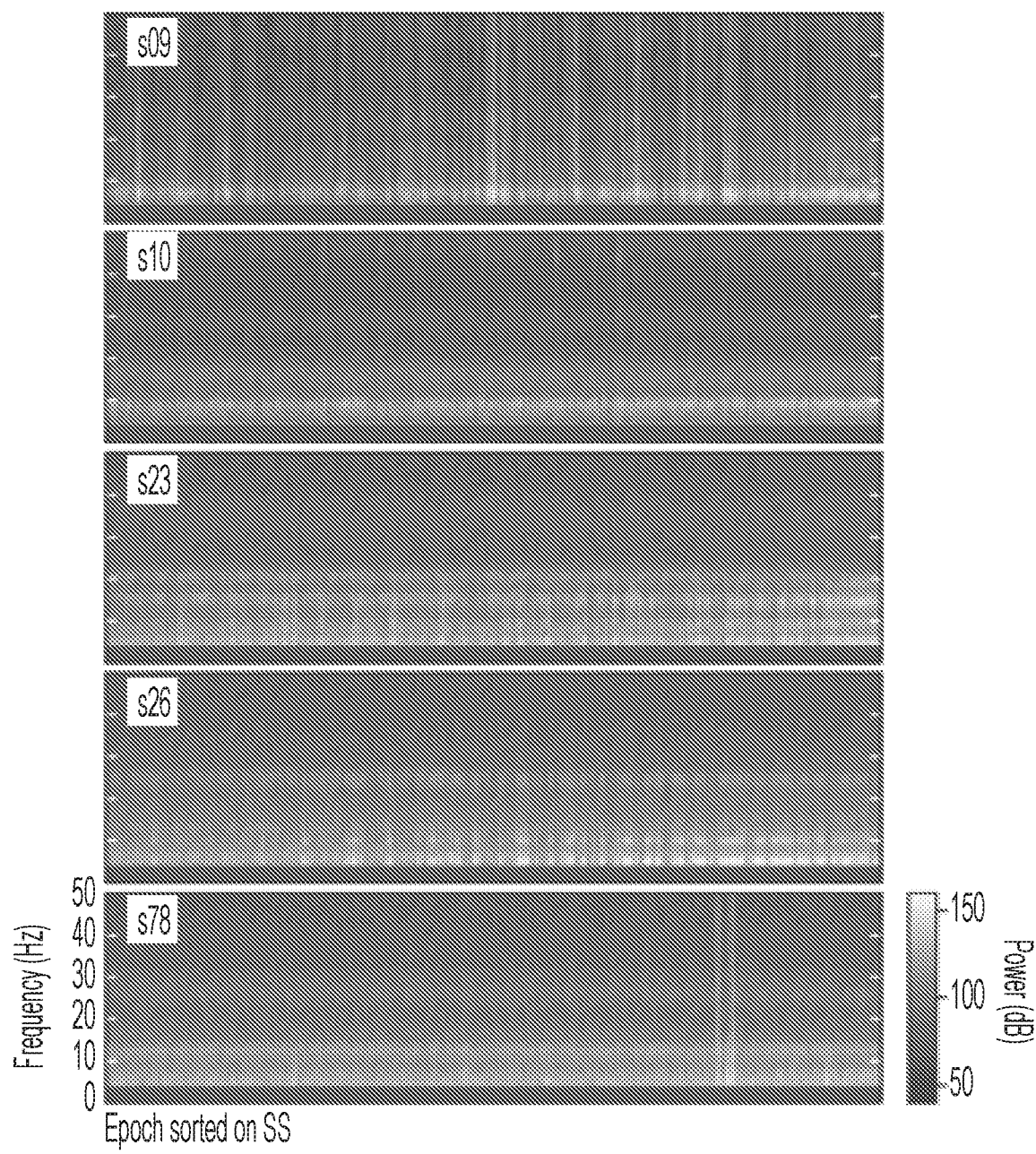

Oscillations in the β frequency band are considered a likely biomarker for PD symptom severity, and indeed there was often a correlation between the SS and β-band power (FIG. 4). The distribution of these correlations across all recordings was positively skewed, but the majority of recordings showed low-to-moderate correlations between β and SS (FIG. 4). In fact, correlations of SS with θ and α frequency power were generally of similar magnitude to those with β power, although for particular neural recordings one frequency range may have been more strongly correlated than the other (FIG. 4). In other words, for some signals β oscillations were well-correlated with SS, whereas for others θ or α oscillations were more closely tied to the 3-second SS. To determine if higher frequency bands might be related to short timescale motor fluctuation, we examined the correlation between gamma and high gamma activity (up to 400 Hz) and SS (4-200 Hz shown in FIG. 4). Lower average correlation values were observed for these bands across all recordings, though these were nonetheless significantly above zero. The average correlation for wide-band power from 4-400 Hz with SS was similar to that for θ/α and β power.

Figure 5:
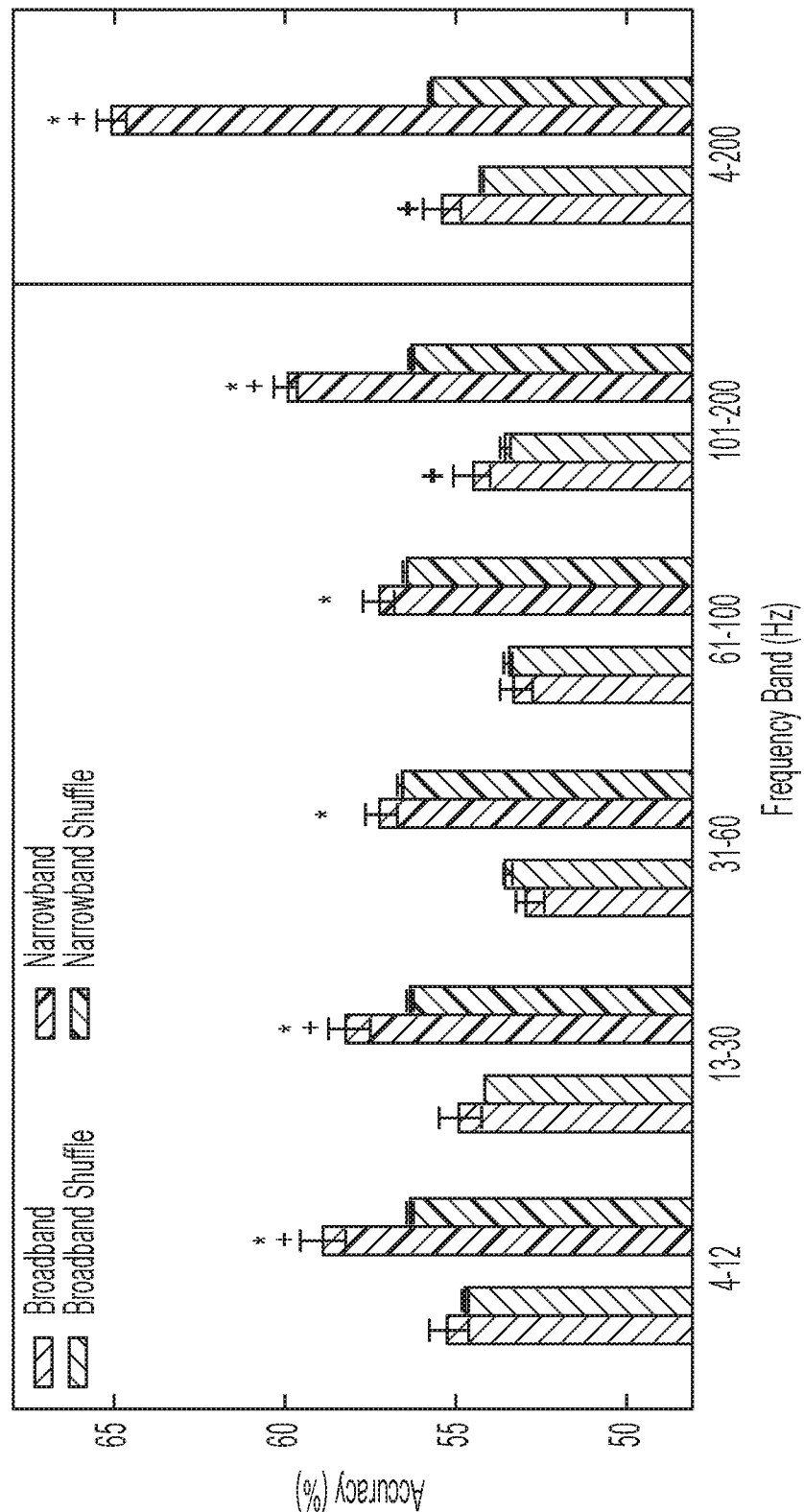
FIG. 5 illustrates an exemplary Neural SVM.
Figure 5:
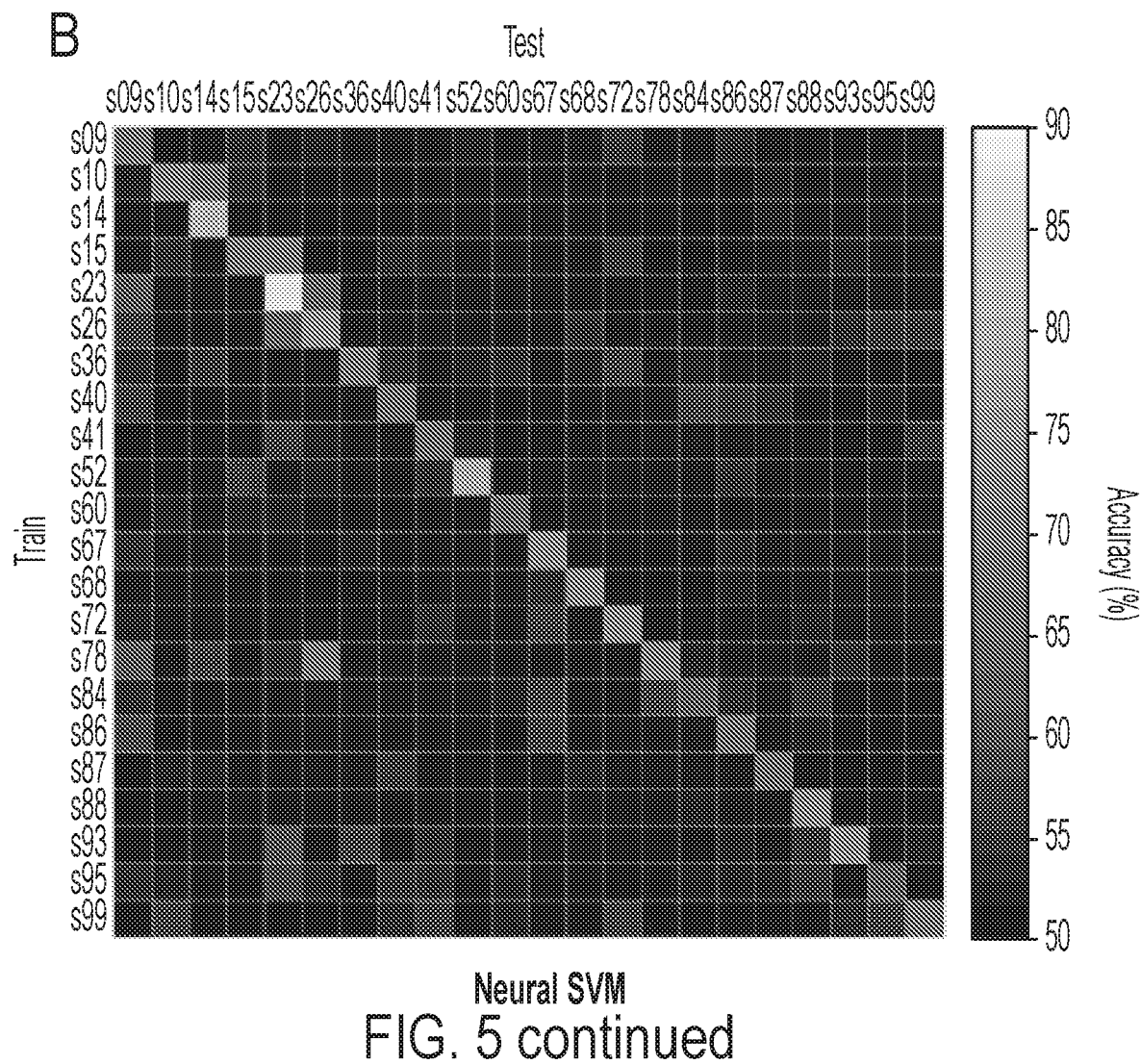
Figure 5:
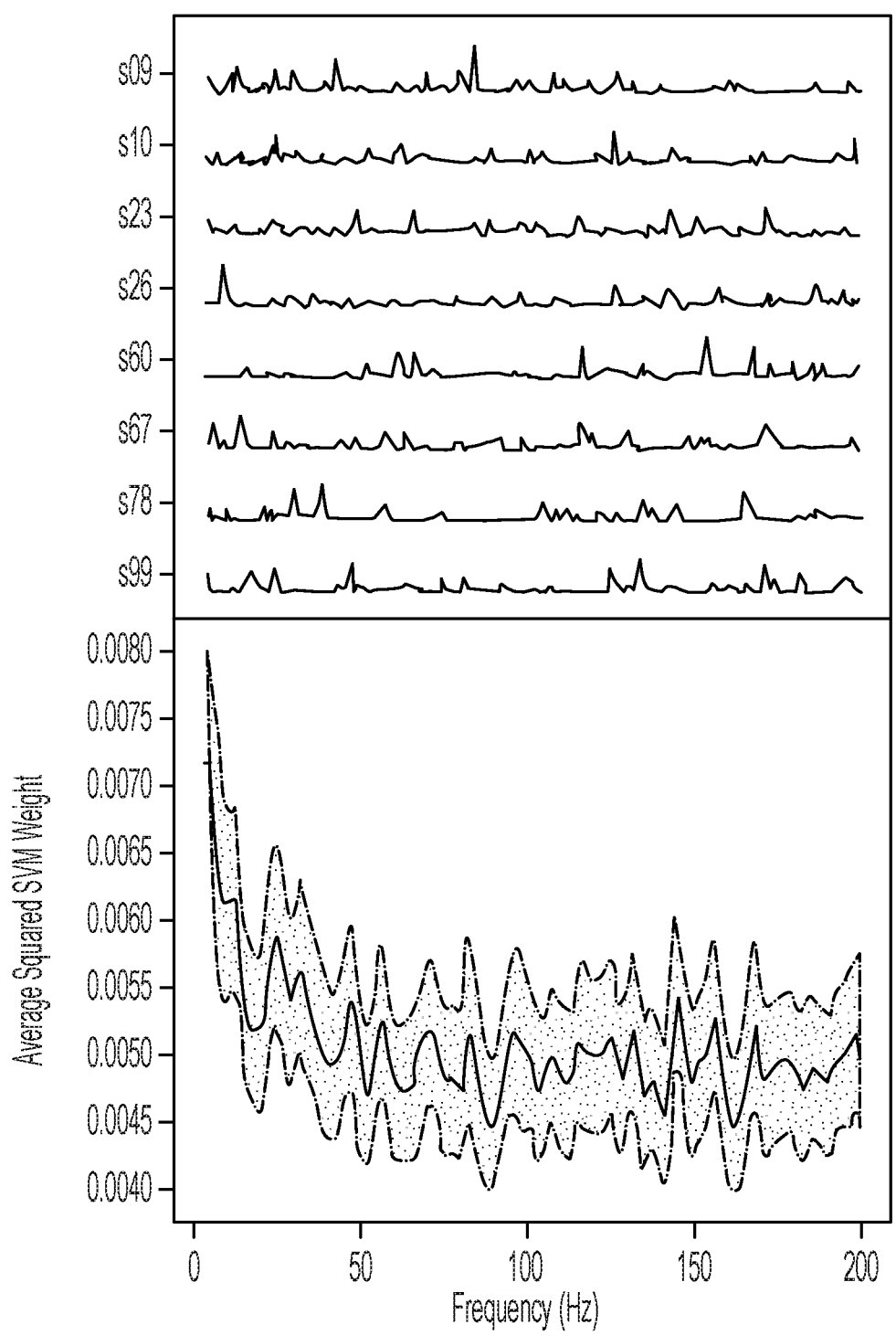
Figure 5:
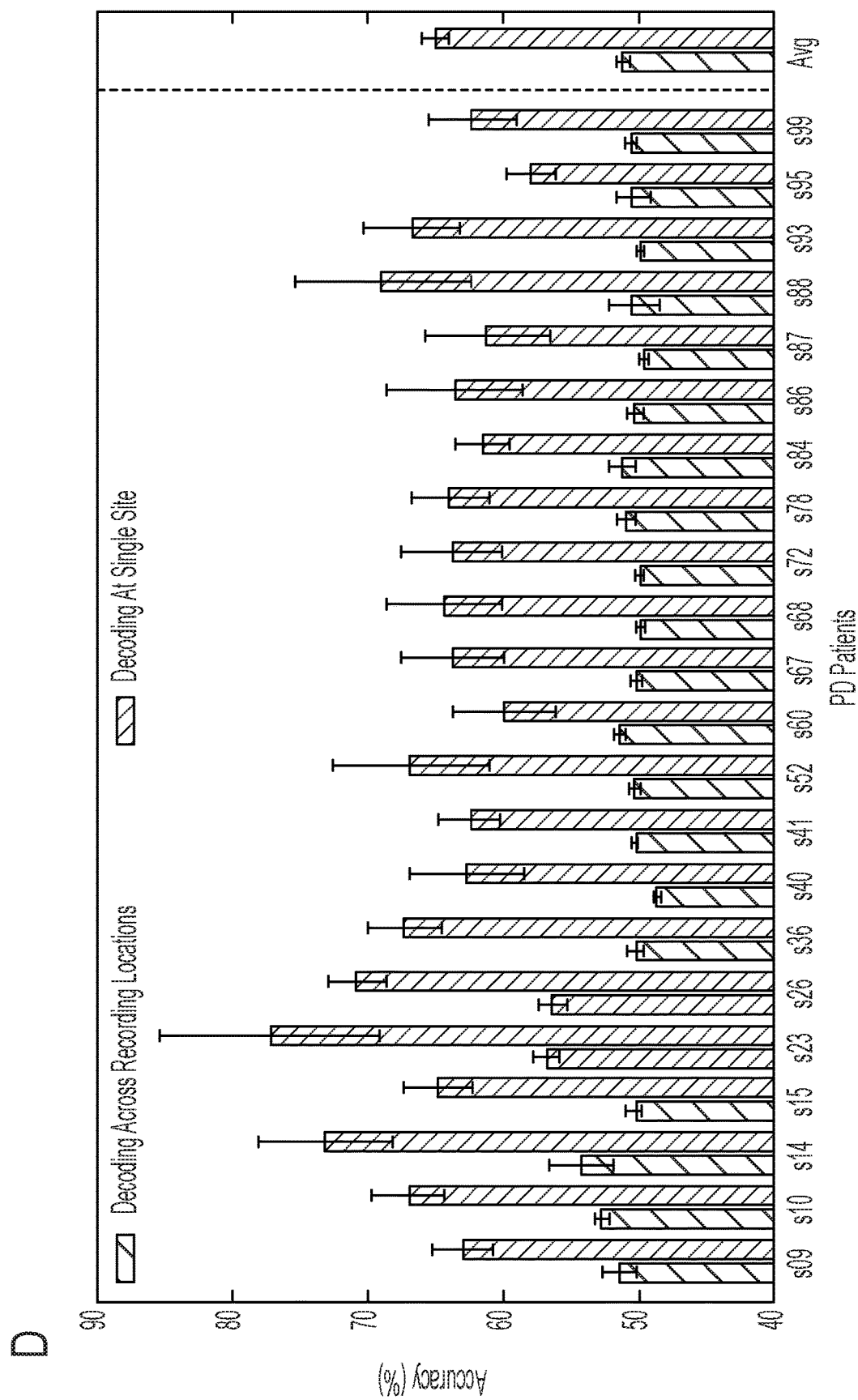
Figure 5:
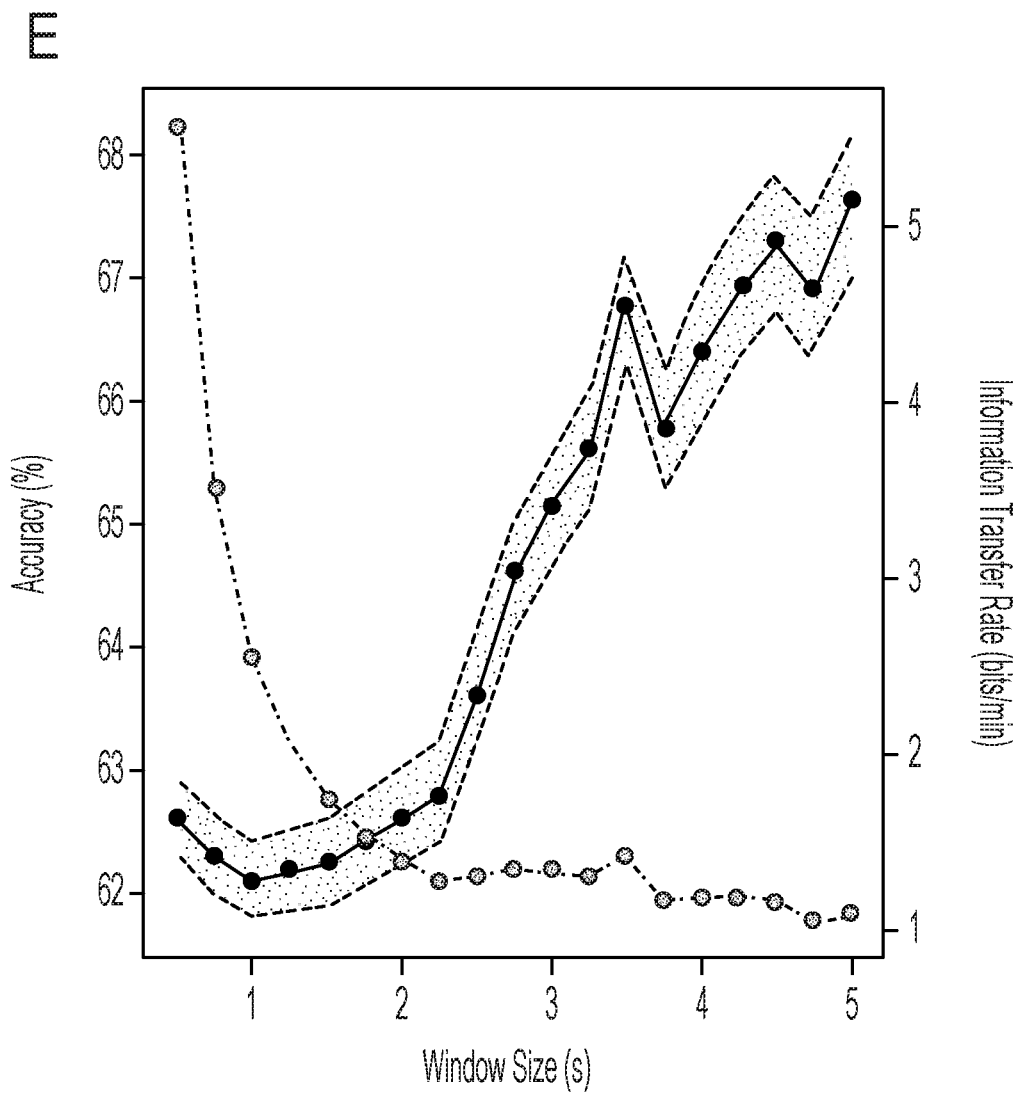

To assess the relationship between oscillatory power and motor impairment more broadly, the LFP spectrogram from 4 to 200 Hz was calculated for comparison to the SS (FIG. 4). Arranging 3-second epochs of the spectrogram according to the corresponding SS yielded visible patterns of neural activity organized by the severity of motor impairment within these short timescales (FIG. 4), with typically increased oscillatory power in particular frequencies as SS increased. We next calculated the correlations between oscillatory power in small frequency bands (2 Hz bandwidth) and SS. This suggested that, on average, the lowest frequencies (up to ~30 Hz) showed the greatest correlations with SS (FIG. 5A). However, examining recordings from individual subjects with PD revealed that the particular patterns of correlations varied (FIG. 5B), with potentially significant positive and negative correlations throughout the entire frequency range.

Classification of Symptom Severity using STN LFPs

We next sought to determine if STN neural activity could be used to distinguish epochs of high vs. low motor impairment. An SVM classifier was created to assess which neural features (here, the power in particular frequency bands) best enabled classification of the 3-second SS as simply high or low (top vs. bottom 50% of SS scores). The data were separated into training and testing portions (90% vs. 10%) and 10-fold cross validation was performed.

Figure 6:
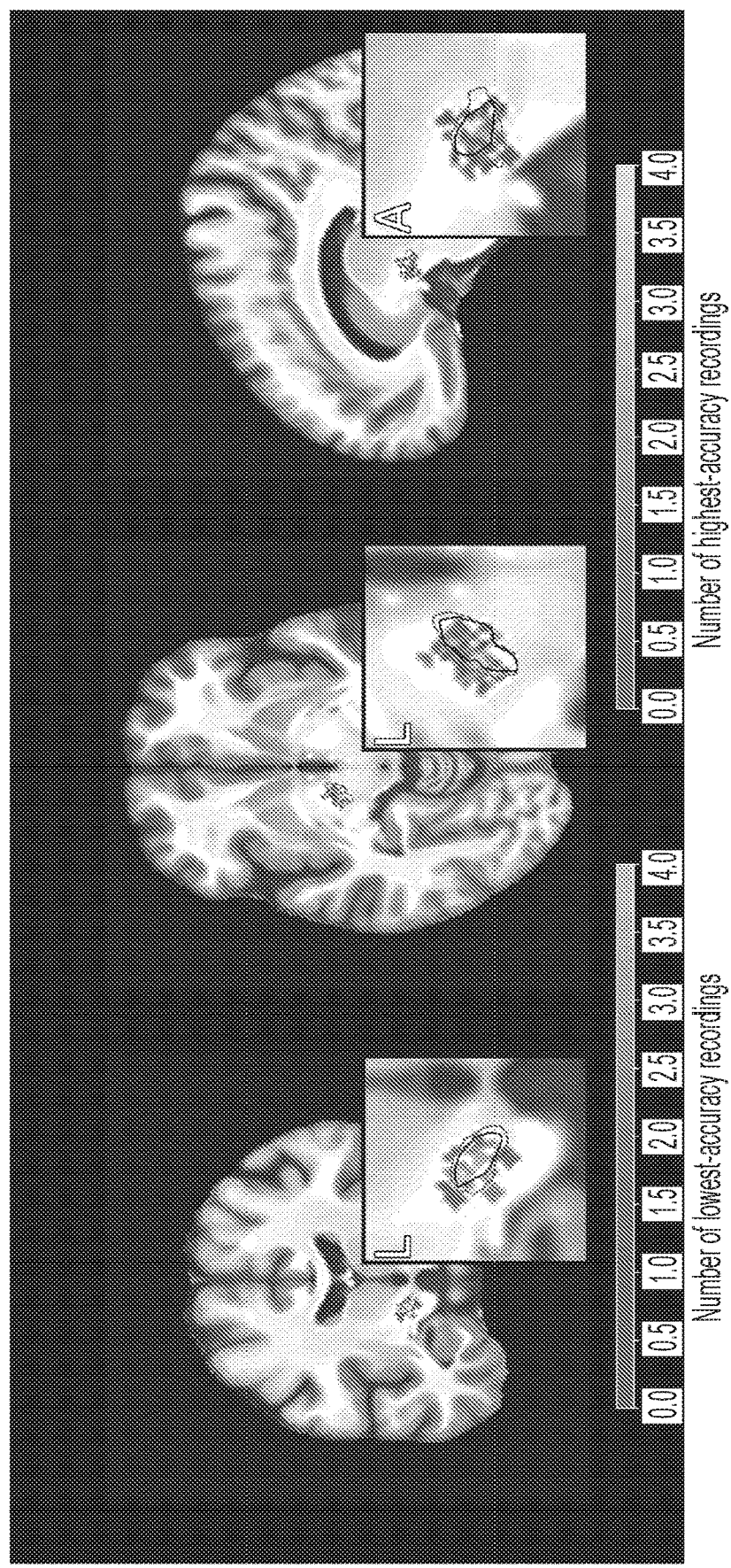
FIG. 6 illustrates exemplary recording locations.

Initially, symptom severity classification was performed using simply the power of oscillations within broad, canonical frequency bands (θ/α: 4-12 Hz; β: 13-30 Hz; low gamma: 31-60 Hz; mid-gamma: 61-100 Hz; and high gamma: 101-200 Hz). This yielded classification accuracies modestly above chance primarily with the lower and higher frequencies (FIG. 6A, dark red bars). Importantly, when compared to a bootstrap statistical procedure that shuffled the assignment of SS to LFP spectral epochs (light red bars), classification accuracy using the broad, canonical frequency bands was not generally significantly better. In contrast, using finer grained neural spectral features (2 Hz frequency windows tiling the entire range of 4-200 Hz in 1 Hz steps; dark blue bars) significantly boosted classification accuracy above that obtained with the broader bands and above that obtained with the shuffled control (light blue bars), indicating more precise information about motor error was available in narrower subcomponents of the canonical frequency bands. The average SVM weights across all frequencies tended to emphasize the lower frequencies (FIG. 6B). However, as for the simple correlations of SS with spectral power at different frequencies, the pattern of weights generated by SVM classifiers were different across individual patients (FIG. 6C). Indeed, applying classifiers trained on one patient's data to another's ("homologous" condition) typically resulted in significantly lower classification accuracy than when applied to the same patient's data ("autologous" condition). Even when this cross-decoding procedure was applied to different recordings within single patients across sites, significant heterogeneity in the informative figures resulted in low accuracy when classifiers trained on neural signals from one location were applied to decode the SS using signals obtained from a separate location. These results demonstrate that the micro-LFP signature of motor impairment varied widely both across and within patients, giving rise to the key feature of this invention which is to not only use patient-specific behavioral measures, but to use these to identify patient-specific neurophysiological biomarkers.

In addition to classification, neural signals can be used in a similar manner to estimate motor fluctuations in a more continuous fashion. Applying non-linear support vector regression to neural signals derived from the STN to decode the SS, for example, yielded estimates of motor fluctuations on the 7-second timescale ranging from ~0.2 to 0.8, depending on the patient and the particular recorded neural signal. Some instantiations of this invention may therefore use graded estimates of motor fluctuations rather than binary classification.

To understand how different temporal window sizes influenced SS classification accuracy, we tested epochs from 500 to 10,000 milliseconds and observed a generally monotonic improvement in classification accuracy with larger windows (500 to 5000 ms shown in FIG. 6G). However, the additional information gained per unit time dropped off rapidly over the first two seconds (FIG. 6H). These results demonstrate a trade-off between accuracy and timescale that would be relevant for applications that leverage short-timescale symptom severity classification, such as closed-loop DBS.

Figure 7:
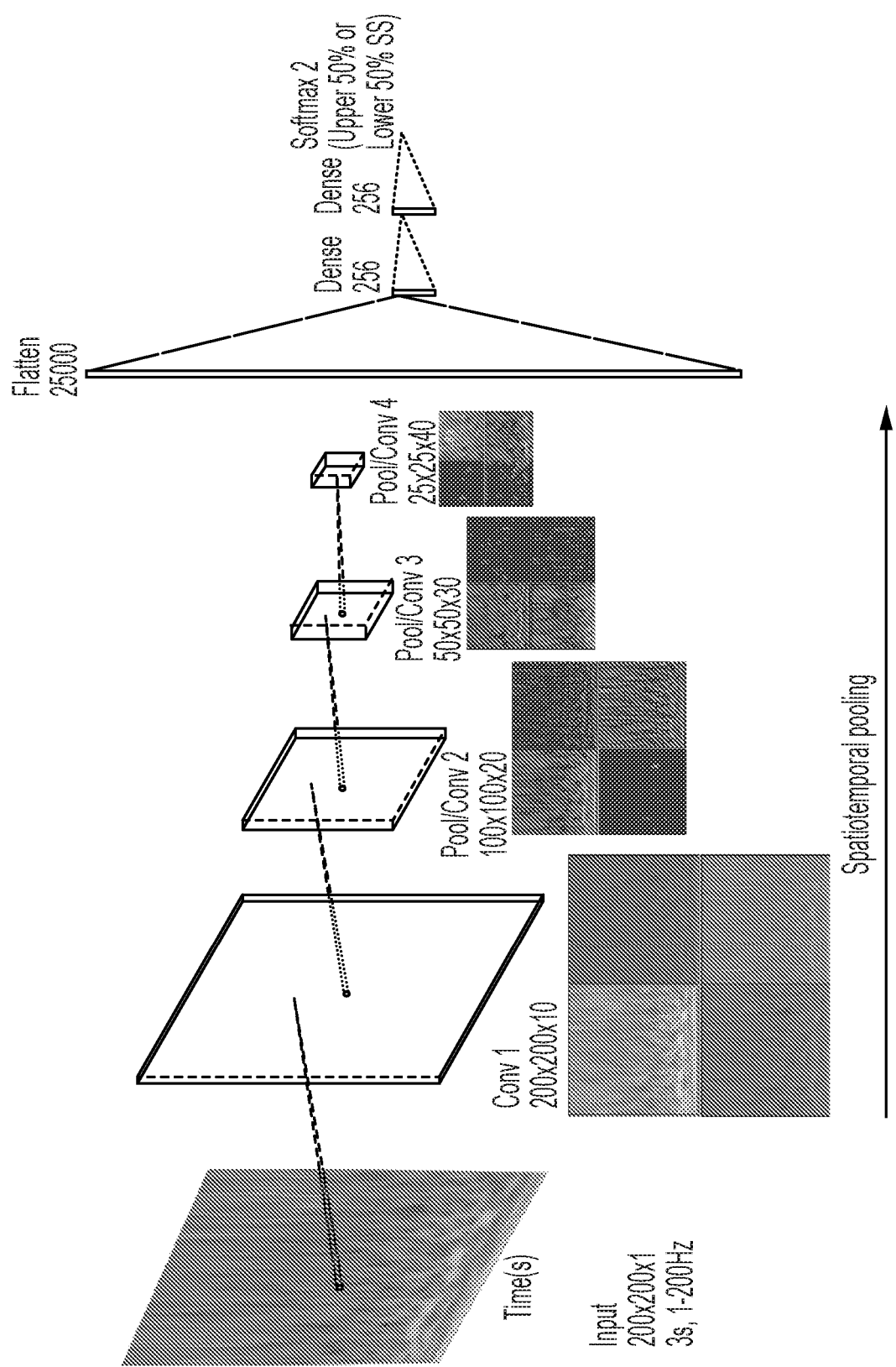
FIG. 7 illustrates an exemplary CNN.
Figure 7:
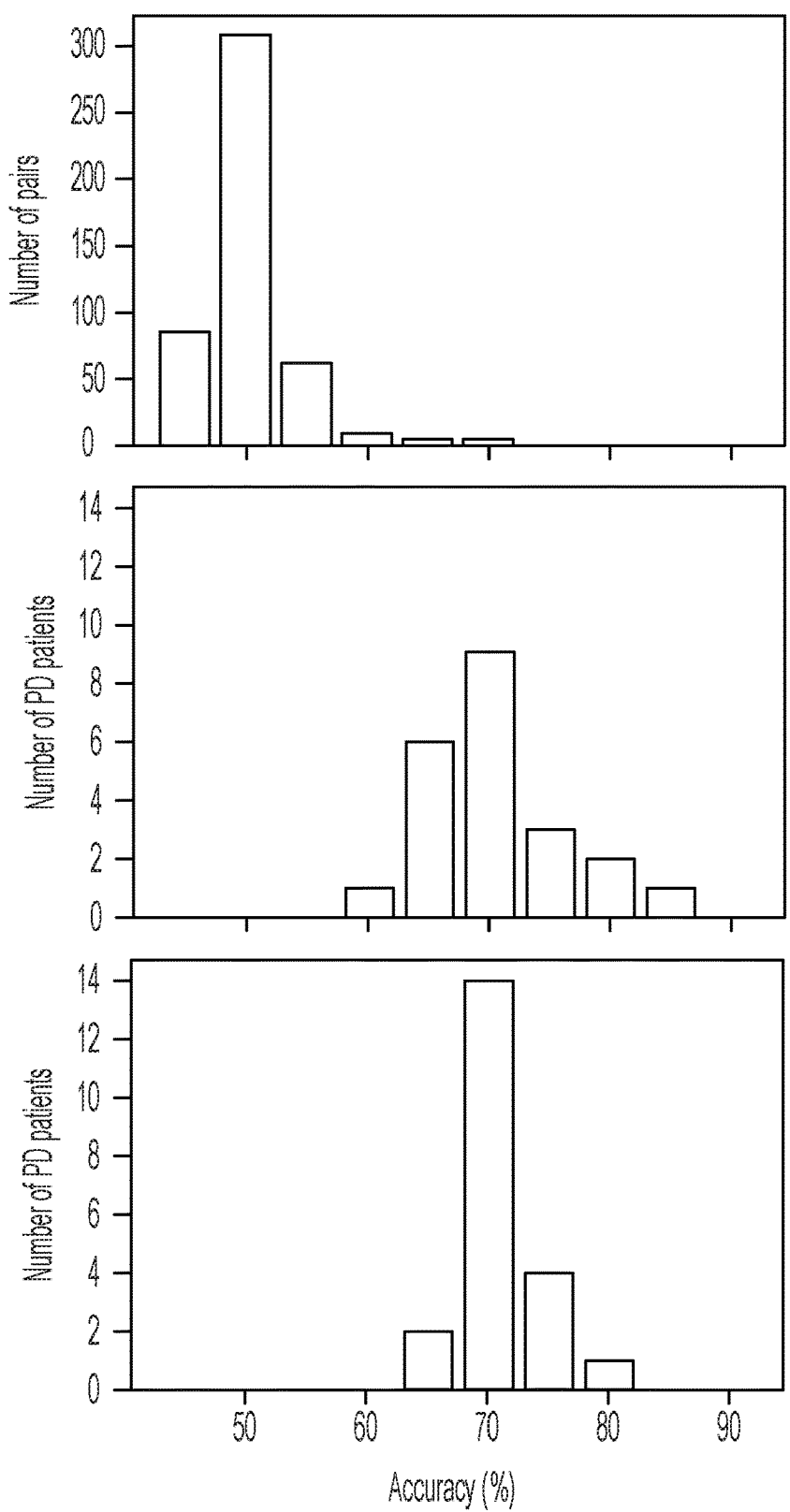
Figure 7:
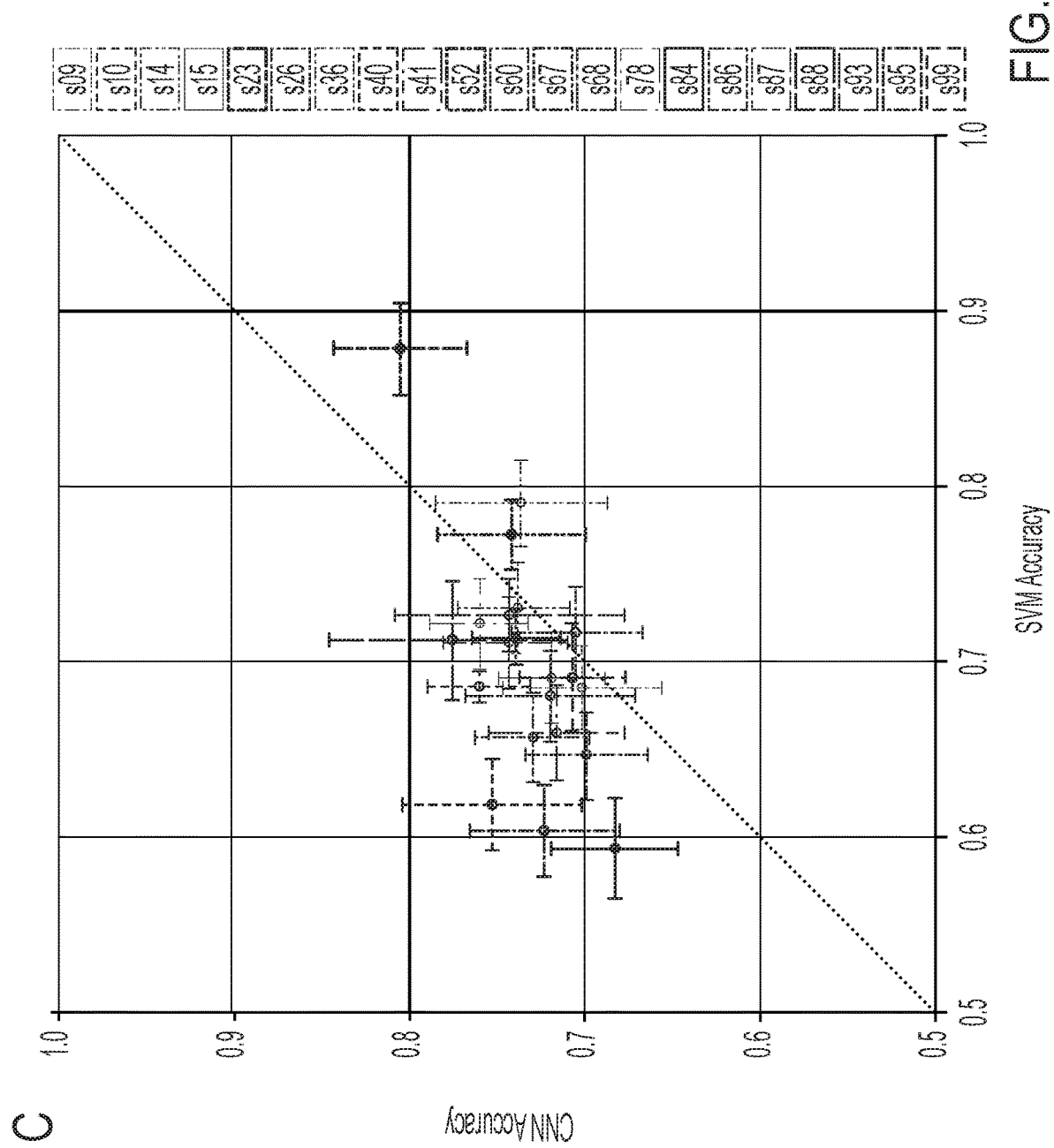

We next sought to determine where the most informative signals were located with respect to the STN. Imaging necessary to accurately reconstruct intra-operative recording locations was available for 20 of 22 patients (140 of 152 recordings). We determined for each patient the coordinates of the recordings that yielded the best and worst SS classification accuracy by SVM and plotted these two points for all patients on a normalized neuroanatomical atlas (FIG. 7X). This approach preserved within-subject topography and reduced potential error related to the co-registration of individual brain images to a single atlas. Here, we observed that the recording locations yielding neural signals that supported the highest classification accuracies clustered primarily in the dorsolateral STN, consistent with localization in the sensorimotor subdivision which is typically considered the optimal target for DBS therapeutic effect.

Figure 8:
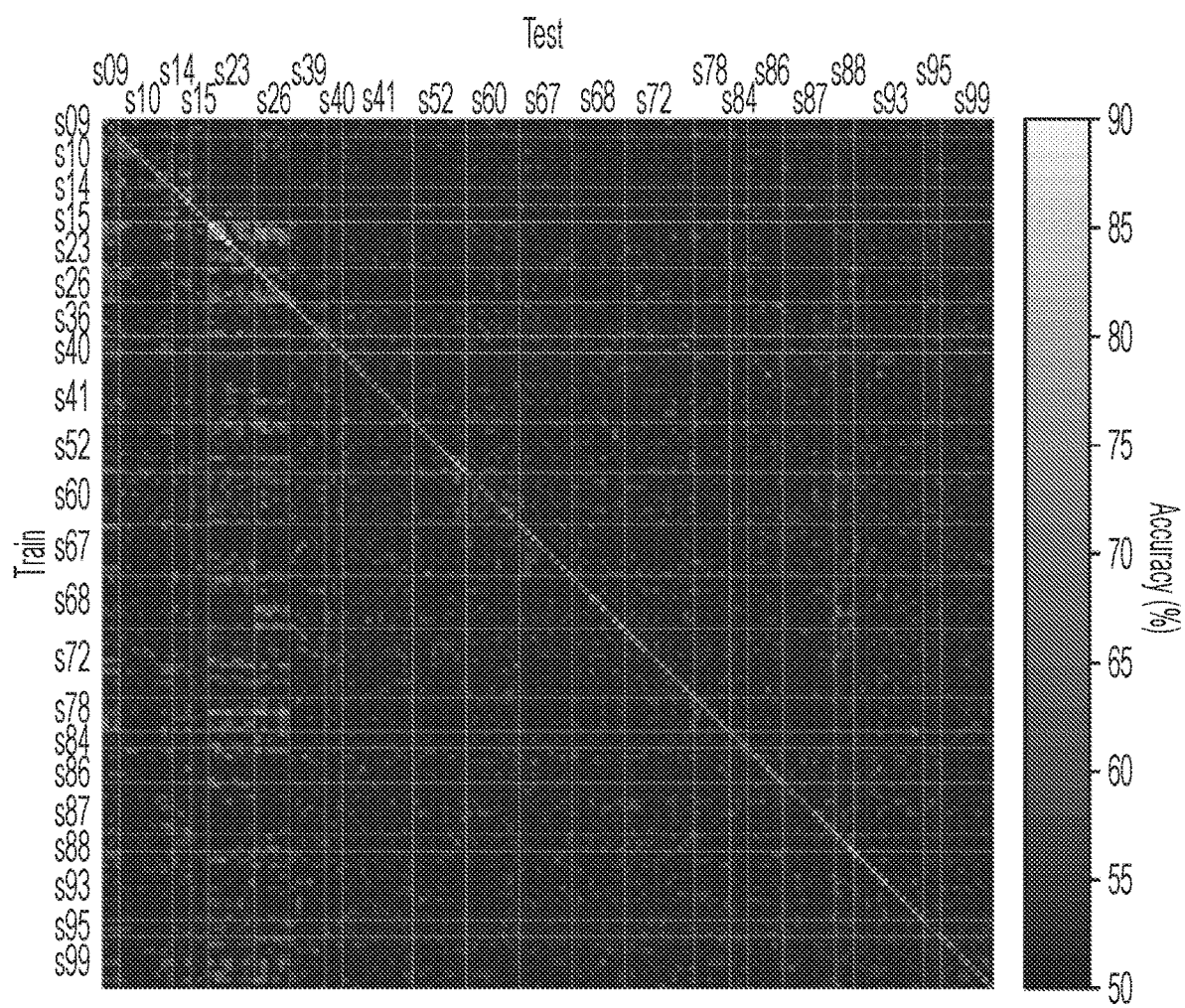
FIG. 8 illustrates an exemplary confusion matrix for all recordings.
Figure 9:
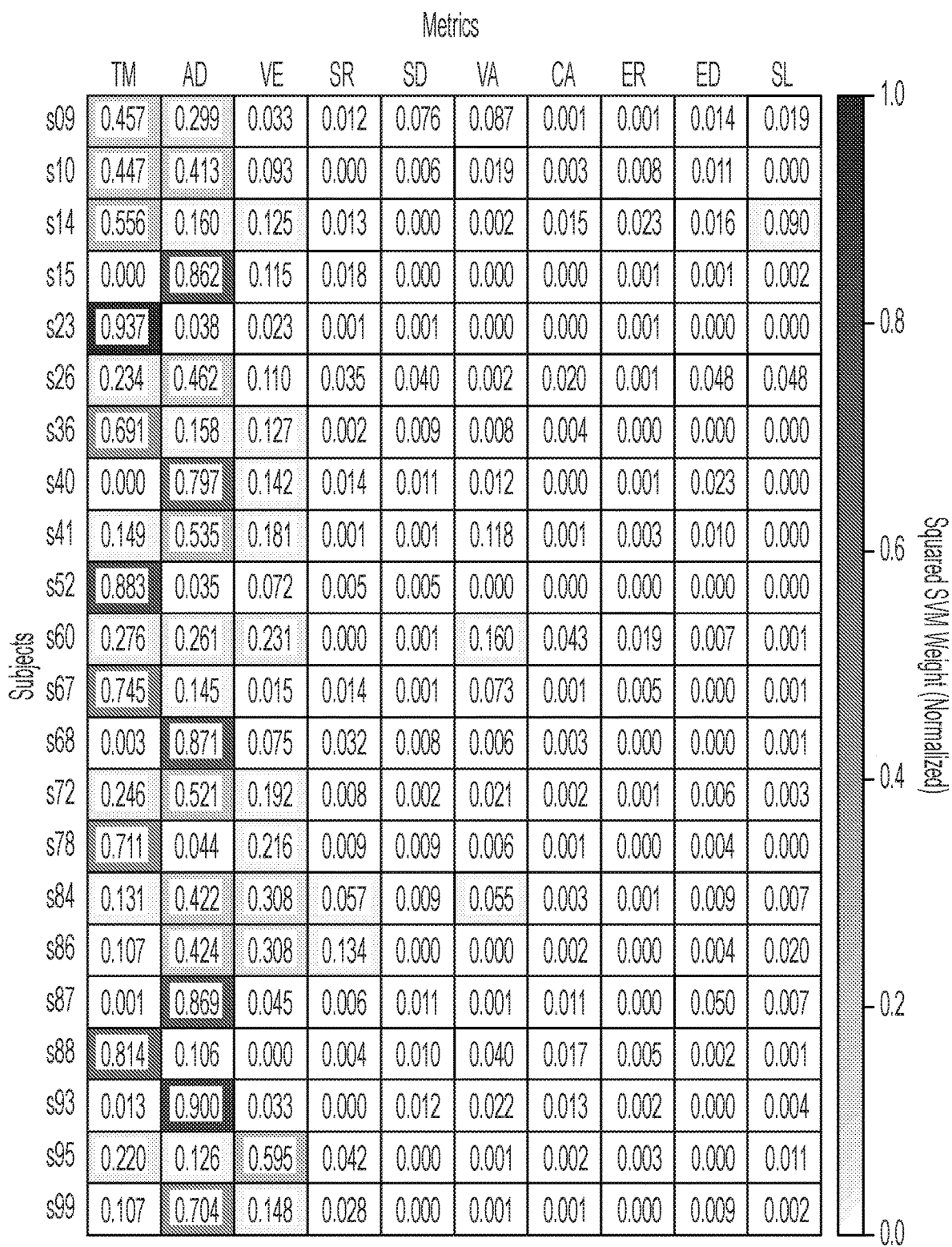
FIG. 9 illustrates an exemplary table of SVM weights.
Figure 10:
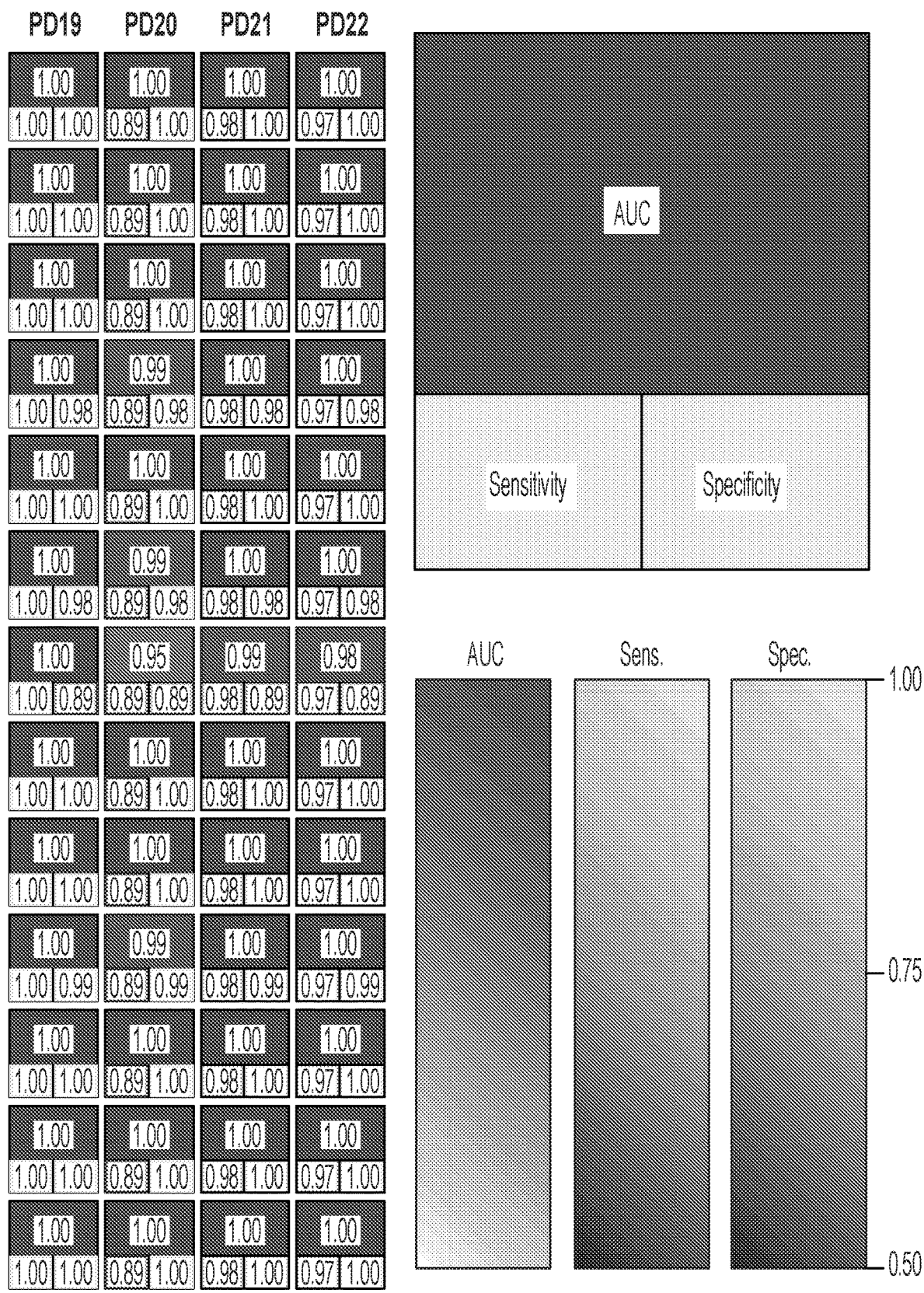
FIG. 10 illustrates exemplary AUC/Sensitivity/Specificity.

The advantage of the SVM classifier is its relative simplicity: it determines the optimal linear boundary between groups in feature-space and the weights on each feature used to create this boundary can be directly and easily reviewed. However, other instantiations of this invention may apply different machine learning methods to boost classification and regression accuracy when knowledge of the specific features weights is not needed. To demonstrate this, we employed an artificial convolutional neural network (CNN). We trained a CNN to classify SS as high vs. low in a similar fashion as the SVM (FIG. 8A). The LFP spectrogram was provided as input in the form of "images" consisting of 3-second epochs across 4-200 Hz of bandwidth in 1 Hz steps, each labeled with the corresponding SS. The data were split into training and testing fractions with 10-fold cross validation as for the SVM. Indeed, we found that SS classification accuracy improved with the CNN compared to the SVM in 20 of 22 patients (FIG. 8B,C), suggesting there were additional informative features within the simple spectrogram related to short timescale motor symptom severity.

To summarize, the present invention is a continuous, rapid assay of motor performance in order to understand the neural correlates of PD symptoms on short timescales. We found that the spectral features of neural signals from the basal ganglia did indeed correlate with rapidly fluctuating behavior, and that these features could be used to classify motor impairment on the timescale of only a few seconds. We observed that frequency bands outside of $\beta$ were often correlated with SS, and that narrow frequency bands within the broader canonical bands contained useful information about short timescale symptom severity. Further, machine learning algorithms (SVM and CNN) were able to use simple spectral features of the LFP to classify or estimate motor symptoms at short (3-second) time scales. This link between neural rhythms and symptom severity on these short timescales strengthens the hypothesis that pathologically increased oscillations may underlie motor impairment in PD.

Prior work has compared on-therapy vs. off-therapy states using simple tasks such as repetitive stepping or finger tapping as quantifiable, relatively short-timescale surrogate measures for PD, and there is indeed some evidence to support the notion that movement metrics derived from rhythmic, distal, fine motor tasks are correlated with UPDRS scores and can yield reasonable sensitivity and specificity for the diagnosis of PD. In contrast, we examined rapid, endogenous fluctuations in motor performance using a task designed to elicit goal-directed motor behavior such that deviations from the intended target could easily be observed and quantified in order to more precisely estimate motor impairment due to Parkinsonian symptoms. Our approach succeeded in discriminating between subjects and controls in a highly accurate manner, and in organizing neural activity in a sufficiently meaningful way that it could be examined to decode symptomatic state in a simple, binary fashion. The accuracy of symptom state decoding varied widely across patients, ranging from about 60% to nearly 90% in one case, with most cases around 70-75% correct. An important limitation of the particular approach employed here is that classifying a continuous distribution of SS into binary groups will have difficulty near the arbitrary discrimination threshold, especially in the presence of noise. Alternative approaches to estimate SS in a more parametric fashion are also feasible, and may be employed in particular instantiations of this invention.

The precise pattern of informative oscillations varied across individuals. Some of this may reflect anatomical differences (inexact correspondence of STN subregions recorded across patients). For example, the distributions of $\beta$ and alpha activities may differ topographically across the STN. In the current work, neural recordings were performed opportunistically when the operative procedure allowed; this may have been in part responsible for the variability of symptom state decoding accuracy and feature weights across patients, though our findings nevertheless demonstrate information about SS was distributed throughout this region in a potentially broad range of frequency bands. Alternatively, or in addition, some of the variation may reflect the particular symptomatic phenotype. However, the very low success rates of SS cross-decoding across all pairs among the 152 neural recordings suggests that perhaps the heterogeneity reflects the idiosyncratic complexity of individual neuronal circuits.

Recently, $\beta$ bursts in a time-limited window preceding movement were observed to be associated with impaired movement dynamics. The work presented here is in general agreement with the view that $\beta$ oscillations are linked to motor impairment, though to widely varying extents across different recordings and individuals. Furthermore, our observation that $\beta$ sub-bands may provide additional information is broadly consistent with prior reports arguing for a distinction between high vs. low $\beta$ activity, though this had been assessed previously only over longer timescales, in the medication on vs. off states. We extend this idea to show that narrower frequency bands may be more informative throughout the tested spectrum (up to 200 Hz). One potentially important difference between our recordings and those in prior work is our use of microelectrode-derived LFP signals rather than macro-electrode (typically DBS electrode) LFPs; micro-LFP recordings are more likely to detect spatially restricted signals.

The notion that frequency bands adjacent to $\beta$ may play some role in the pathophysiology of PD already has some longer timescale experimental support. Single unit spiking in the sub-$\beta$ band (2-13 Hz) has been reported to correlate with axial and limb rigidity, whereas spiking in the low-gamma range (40-90 Hz) was observed to negatively correlate with bradykinesia. Our results are consistent with the notion that activity outside the $\beta$ range may be important, and we did observe negative correlations between oscillatory power and symptom severity in some cases for a variety of frequency bands. What was surprising, however, was the significant individual variability and the degree of dependence on frequencies well outside the β range, especially in the "high gamma" range that is reflective of multi-unit neuronal spiking. Gamma band activity in a more restricted range (60-90 Hz) has been associated with dyskinesias; however, our subjects were off medication while undergoing the DBS electrode implantation procedure, so would not have exhibited dyskinesias. Therefore, any weighting of that frequency band by our classification algorithms was unlikely related to that particular type of medication-induced motor symptom. The wide range of frequency bands and broad anatomical areas observed to contribute information about motor performance could, to some extent, reflect cognitive processing related to the evaluation, recognition or attempted correction of motor errors.

For both the SVM and CNN machine learning approaches, we restricted the input feature space to LFP power at different frequencies. This ignores significant information that may be present in the phases of these oscillations, particularly when combined with amplitude information. In addition, we restricted our analysis to classifying symptoms in a binary fashion (high vs. low). Further optimization of the feature sets and algorithms may allow higher accuracy and more graded estimations of symptom severity, and would be consistent with the general approach of this invention.

Short time scale neurophysiological biomarkers of PD symptoms have several potential practical applications, including objective symptom tracking and responsive neuromodulation. For example, closed-loop DBS, in which stimulation is dynamically delivered as needed, requires a control signal that reflects the immediate or impending presence of symptoms. Our results suggest that current strategies that focus simply on broad β-band activity may be suboptimal, and not fully generalizable across patients and STN sites. Note also that STN β decreases just before and during movement, so its use as a control signal for PD motor symptoms during ongoing behavior might be suboptimal. Furthermore, β oscillations are not necessarily pathological, even in Parkinsonism, so stimulating simply to disrupt β might have unanticipated adverse influences on motor behavior. This and other work have suggested that targeting longer β episodes might more selectively address Parkinsonian symptoms. We show here that using a combination of patient-specific neural oscillations that are specifically tied to the moment-to-moment expression of motor symptoms might further refine the strategy for implementing closed-loop DBS. A better understanding of the links between broadband neural activity and symptoms, and knowledge of the algorithms needed to fully exploit these links, can guide the design of more advanced devices to realize the potential of closed-loop neuromodulation for optimal patient benefit.

Subjects

Patients undergoing routine, awake placement of deep brain stimulating electrodes for intractable, idiopathic Parkinson's Disease were invited to participate in this study. PD patients were selected and offered the surgery by a multidisciplinary team based solely upon clinical criteria, and the choice of the target (STN vs. Globus Pallidus internus) was made according to each patient's particular circumstance (symptoms and goals). Here we focus on just those patients undergoing STN DB S (n=22). Patients were off all anti-Parkinsonian medications for at least 12 hours in advance of the surgical procedure. Approximately age-matched controls (often patients' spouses or partners) also participated in this study (n=15); controls were required simply to be free of any diagnosed or suspected movement disorder, and to have no physical limitation preventing them from seeing the display or manipulating the joystick. Patients and other subjects agreeing to participate in this study signed informed consent and experimental procedures were undertaken in accordance with an approved Rhode Island Hospital human research protocol (i.e., Lifespan IRB #263157).

Behavioral Task

We employed a target-tracking task to estimate the degree of patient symptoms in a continuous fashion. Specifically, while PD subjects reclined on the operating table in a "lawn-chair" position, a joystick was positioned within their dominant hand and a boom-mounted display was positioned within their direct line-of-sight at a distance of ~2-3 feet. The task was implemented in MonkeyLogic and required subjects to follow a green target circle that moved smoothly around the screen, manipulating the joystick to keep a white cursor within it. The target circle followed one of several possible paths (invisible to the subject), with each trial lasting a number of seconds. Each session consisted of multiple trials (several minutes of tracking data), and subjects performed 1-4 sessions during the surgery. Control subjects performed this task in an extra-operative clinic setting.

Motor Metrics

Several measures of motor performance were applied to this task in small time windows (3 second epochs with 50% overlap). These measures consisted of tremor (the magnitude of the 3-8 Hz band-pass filtered x- and y joystick traces) and other metrics calculated after low-pass filtering the x- and y-joystick traces below 3 Hz. These library of metrics demonstrated here included tremor (T) and: distance (D), vector error (VE), vector ratio (VR), vector difference (VD), vector angle (VA), excursion ratio (ER), tracking angle (TA), excursion difference (ED), and slowness (S), though other metrics may be substituted so long as the correlation with the remaining set is relatively low, allowing motor error to be more fully captured across a broad feature space. Because the motor manifestations of PD are heterogenous, for each PD subject, we sought to determine the combination of weights that maximally captured their individual motor symptoms. To exemplify this, we applied a support vector machine (SVM) algorithm to define the hyperplane in the 10-dimensional metric-space that optimally separated a PD subject's performance from that of controls. The SVM was calculated 1000 times using an equal number of randomly-selected control data points, matched to the number of PD subject data points; the average hyperplane was then used for subsequent analyses. The parameters defining this hyperplane corresponded to the weights applied to the different metrics. The Euclidean distance from each of a PD subject's data points to the hyperplane was defined as the instantaneous "symptom score" (SS). The average SS across a session or across sessions within a patient were calculated in a straightforward fashion from these individual values.

Surgical Procedure

Microelectrode recordings (MER) from the region of the STN of awake patients are routinely performed in order to map the target region and select the best position for DBS electrode implantation. The initial trajectory was determined on high-resolution (typically 3T) magnetic resonance (MR) images co-registered with CT images showing skull-anchor fiducial markers. A 3-D printed stereotactic platform (STarFix micro-targeting system, FHC Inc., Bowdoin, ME) was then created such that it could be affixed to these anchors, providing a precise trajectory to each target. Microdrives were attached to the platform and microelectrodes were then loaded. Recordings were typically conducted along the anterior, center and posterior trajectories (with respect to the initial MR-determined trajectory) separated by 2 mm, corresponding to the axis of highest anatomical uncertainty based upon the limited visualization of the STN on MR imaging. MER began about 10-11 mm above the MM-estimated target, which was chosen to lie near the inferior margin of the STN, about ⅔ of the distance laterally from its medial border. The STN was identified electrophysiologically as a hyperactive region typically first encountered about 2-5 mm above estimated target. At variable intervals, electrode movement was paused in order to assess neural activity and determine somatotopic correspondence, as per routine clinical practice. At these times, if patients were willing and able, additional recordings were obtained in conjunction with patient performance of the visual-motor task. Other instantiations of this invention could use different types of electrodes to record neural signals (most notable, deep brain stimulating electrodes), and can obtain those signals from different portions of the basal ganglia.

Neurophysiological Signals & Analysis

In the demonstrated instantiation, once at least one electrode had entered the STN (determined by a combination of increased background activity, frequent bursting of single units, and often audible beta oscillations and/or somatotopic correspondence of activity with passive limb movements), patients were asked to perform the target tracking task. Neural signals from the first 2 patients were acquired with FHC tungsten electrodes and an FHC data acquisition system (FHC Inc., Bowdoin, ME, USA) with signals split into a Plexon MAP system (Plexon Inc., Dallas, TX, USA); data for the subsequent 20 patients were recorded using "NeuroProbe" tungsten electrodes and Neuro Omega systems (Alpha Omega, Inc., Nazareth, Israel). Electrode impedances were typically 400-700 k$\Omega$.

Patients performed up to 4 sessions of the task, with electrodes positioned at different depths for each session. Behavioral data across sessions from individual subjects were combined to calculate of the SVM to generate the SS classifier. Once the metric weights for the SS were determined, data were analyzed within individual sessions corresponding to unique sets of recording locations.

Data were analyzed in MATLAB® (Mathworks, Natick, MA). Neural signals from the microelectrodes were initially acquired at 40-44 kHz, then downsampled to 1 kHz and bandpass filtered from X to X Hz to obtain the micro local field potentials (LFPs). LFPs were bandpass filtered within particular frequency ranges of interest using a Fast Fourier Transform (FFT) in each 3-second time epoch. The power in this band was calculated by multiplying the conjugate of the Hilbert Transform by the filtered signal, and this was then expressed as a fraction of the total power in the broader 4-100 Hz band. Depending on the particular analysis, canonical frequency bands (e.g., $\beta \stackrel{def}{=} 13\text{-}30$ Hz range) or smaller frequency bands (consecutive 2 Hz bands with 50% overlap) were used, as described below.

One goal was to determine which spectral features best corresponded with the SS on short timescales (corresponding 3 second epochs of task performance and neural data acquisition). Most simply, the correlation of SS with LFP power in particular frequency bands was calculated. However, we wished to understand if a combination of spectral features might serve as a better biomarker for SS, so classification of epochs as having high or low SS was undertaken with a second SVM using the simple spectral features of the LFP signals. For any particular set of spectral features, the SVM was trained and the squared magnitudes of the SVM weights were normalized by its total power to assess the contribution of particular frequency bands. SVM classification accuracy was assessed with 10-fold Monte Carlo cross-validation across each relevant data set. To demonstrate graded estimation of motor fluctuations, we employed a support vector regression with a non-linear kernel.

Artificial Neural Network Implementation

Convolutional neural network (CNN) analysis was performed using the Tensorflow library (tensorflow.org) with Python 3.6.5. Networks were trained and evaluated on NVIDIA Titan V GPUs with 12 GB RAM. Spectral features were extracted from the LFP to classify the SS. Specifically, Morlet wavelet filters were applied to the LFPs downsampled to 1 kHz to create a spectrogram at 15 ms time resolution and 1 Hz frequency resolution. The spectrogram was divided into 3000 ms windows and normalized by taking the base-10 log and scaling so that all spectral values were in [0,1]. This resulted in 200×200 pixel images (time× frequency). Each image was cross-referenced to its corresponding epoch's symptom score to generate a classification label. A 90/10 training/validation split was used, segregated on a trial-by-trial basis (as for the SVM). A new training/validation split was used for each realization of cross-validation, and the criteria of maximum validation accuracy was used to choose the best model across epochs.

Our CNN used an architecture similar to AlexNet, which is the basis for many convolutional architectures. The input layer adds Gaussian noise in order to augment the data and to account for some inherent variability in spectral data. The distorted input is fed through four convolutional layers with pooling between to learn temporal and spectral features of each spectrogram window. All neurons were rectified linear units (ReLU) with batch normalization, which has been shown to improve learning rates and reduce the need for dropout neurons. These convolutional layers are followed by two dense layers with dropout neurons to prevent overfitting. Finally, a softmax activation is applied to a dense layer with two neurons, resulting in a binary classification. A grid search was conducted to determine kernel, filter, and stride sizes, resulting in a network with 7 million parameters.

A stochastic gradient descent solver with a Nesterov momentum of 0.8 was used for backpropagation; the momentum was decreased linearly on each epoch. Neuron weights and biases were initialized using the Glorot uniform method. A grid search was performed for hyperparameters, yielding a learning rate of 0.001 with a linear decay.

Anatomical Reconstruction of Recording Sites

Patients typically underwent pre-, intra- and post-operative imaging. Preoperatively, stereotactic protocol MR images were obtained (Seimens Vario 3.0T scanner) that included T1- and T2-weighted sequences (T1: MPRAGE sequence; TR: 2,530 ms, TE: 2.85 ms, matrix size: 512×512, voxels: 0.5×0.5 mm2 in-plane resolution, 224 sagittal slices, 1 mm slice thickness; T2: SPACE sequence, TR: 3,200 ms, TE: 409 ms, matrix size: 512×512, voxels: 0.5×0.5 mm2 in-plane resolution, 224 sagittal slices, 1 mm slice thickness). Preoperative, post-operative, and in most cases intraoperative computed Tomography (CT) scans were also acquired (Extra-Op CT: GE Lightspeed VCT Scanner; Tube voltage: 120 kV, Tube current: 186 mA, data acquisition diameter: 320 mm, reconstruction diameter: 250 mm, matrix size: 512×512 voxels, 0.488×0.488 mm$^2$ in-plane resolution, 267 axial slices, 0.625 mm slice thickness; Intra-Op CT: Mobius Airo scanner, Tube voltage: 120 kV, Tube current: 240 mA, data acquisition diameter: 1,331 mm, reconstruction diameter: 337 mm, matrix size: 512×512 voxels, 0.658× 0.658 mm$^2$ in-plane resolution, 182 axial slices, 1 mm slice thickness). MR and CT images were then fused via linear registration using a mutual information algorithm in the Waypoint Planner software (version 3.0, FHC Inc., Bowdoin, Me., USA). Localization of the target relied upon a combination of direct and indirect targeting, utilizing the visualized STN as well as standard stereotactic coordinates relative to the anterior and posterior commissures. Appropriate trajectories to the target were then selected to avoid critical structures and to maximize the length of intersection with the lateral STN.

Postoperative MR images (Seimens Aera 1.5T scanner, T1: MPRAGE sequence, TR: 2,300 ms, TE: 4.3 ms, matrix size: 256×256 voxels, 1.0×1.0 mm$^2$ in-plane resolution, 183 axial slices, 1 mm slice thickness, specific absorption rate<0.1 W/g) were obtained 1-2 days after the operation to confirm proper final electrode location.

To reconstruct recording locations, MR and CT images were co-registered using the FHC Waypoint Planner software. The raw DICOM images and the linear transform matrices were then exported and applied to reconstructed image volumes using the AFNI command '3dAllineate' bringing them into a common coordinate space. Depths were calculated by combining intraoperative recording depth information with electrode reconstructions obtained from intra- or postoperative images using methods described previously.

To understand the anatomical distribution of recording sites across patients, pre-operative T1-weighted MR images were registered to a T1-weighted MNI reference volume (MNI152_T1_2009c) using AFNI's "3dQwarp" command. The resulting patient-specific transformation was then applied to recording site coordinates. MNI-warped recording coordinates were then tested for their proximity (within 1 mm) to the STN as delineated on the MNI PD25 atlas.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A continuous recording method for diagnosing and/or scoring a severity of one or more symptoms in a subject with Parkinson's Disease (PD) or in a subject suspected of having PD, the method comprising the steps of A-E below:
   (A) placing at least one electrode into the subject's subthalamic nucleus (STN); and using the at least one electrode to apply a neuromodulation via a deep brain stimulation (DBS) to the STN;
   (B) using the at least one electrode for acquiring one or more neural signals from the STN while executing steps (1)-(5) below:
   (1) providing A) an on-screen target to the subject and providing B) a visual cursor to the subject, and a way of moving the cursor; whereby A) and B) are provided with a computer and software capable of continuously measuring and recording a distance between, a direction, and a speed of the target and of the cursor over a short-timescale in the range of 500 ms to 10000 ms;
   (2) moving the on-screen target over the short-timescale, and engaging the subject by requiring the subject to follow the motion of the target with the cursor, whereby the subject attempts to follow said target by moving the cursor in a continuous motor performance task that elicits a motor variability from the subject during the short-timescale;
   (3) using the computer/software to record the distance between, direction, and speed of the target and of the cursor over the short-timescale, and using the recorded distances, directions, and speeds to quantify the motor variability of the subject with one or more metrics that each provide a symptom score (SS) for each metric, wherein the one or more metrics include tremor (T), distance (D), vector error (VE), vector ratio (VR), vector difference (VD), vector angle (VA), excursion ratio (ER), tracking angle (TA), excursion difference (ED), or slowness (S), wherein the one or more metrics are capable to provide an array of motor metrics;
   (4) applying a multi-dimensional classification algorithm to determine weights for each of the symptom scores (SSs) of the one or more metrics, or of the array of metrics, wherein each subject's SSs are compared to SSs of one or more controls subjects performing the same task; and
   (5) combining the weights to determine a first scalar metric of motor performance for each short-timescale; wherein the first scalar metric indicates a score and/or a severity of the one or more symptoms of PD for the subject; and
   executing steps (A) and (B) using another at least one electrode in a different STN position to provide an additional scalar metric;
   (C) combining two or more scalar metrics or SSs to provide a map of scalar metrics or SSs for at least two different STN positions from step (B);
   (D) using a convolutional neural network software to process at least one or more neural signals with a frequency extraction operative to determine a plurality of spectral features for each of the one or more neural signals on short timescales for the at least two different locations in the STN and/or for a motion, behavior, or epoch of the subject; whereby a correlation of SSs with a local field potential power in one or more frequency bands from the plurality of spectral feature is calculated and a diagnosis of the subject is provided including the correlation; and
   (E) controlling the neuromodulation based on the recording method's determination to provide a benefit to the subject's one or more symptoms.

2. The method of claim 1, further comprising the step of measuring an oscillatory power in the basal ganglia of the subject, while the subject performs the continuous motor performance task, and calculating any correlations between oscillatory power in frequency bands of 2 Hz bandwidth and SSs.

3. The method of claim 1, wherein the short-timescale is in the range from 1 second to 10 seconds.

4. The method of claim 2, wherein the method further comprises the step of:
utilizing the method of claim 2 to provide a motor task to quantify rapidly fluctuating motor symptoms of Parkinson's Disease (PD) patients as a basis to identify the corresponding neural biomarkers.

5. The method of claim 4, further comprising applying a support vector machine (SVM) or an artificial convolutional neural network (CNN) machine learning algorithm to neural activity recorded from the basal ganglia to classify and/or estimate motor fluctuations as a subject specific scoring of a symptom severity or of one or more SSs.

6. The method of claim 1, further comprising executing the method using a subject that is known to not have PD and recording the SS for each metric and the scalar metric as a control data; and wherein the control data is operative to differentiate a motor performance from a control subject from a subject with PD or a subject suspected of having PD performing the same method.

7. The method of claim 1, wherein the one or more metrics and/or the array further comprises in addition to the one or more metrics of claim 1 a more specific determination at a single point in time of an absolute distance (AD) between the target and the cursor and time, a Euclidean distance from the target and the cursor and time, a tremor magnitude (TM) of the cursor, a slowness (SL) of the cursor in following the target, a vector error (VE) of the cursor/target, a speed ratio (SR) of the cursor/target, a speed difference (SD) of the cursor/target, a vector angle (VA) of the cursor/target, a correction angle (CA) of the cursor/target, an excursion ratio (ER) of the cursor/target, an excursion difference (ED) of the cursor/target, or a combination thereof.

8. The method of claim 1, further comprising the method is configured as a neural recording method that uses a continuous behavioral/motor task to assess multiple dimensions of a motor disability simultaneously and at the short timescales in order to 1) identify neurophysiological biomarkers of PD; and 2) to assess changes to the programming of the neuromodulation system to improve a performance on a task via a recording of the execution of the method; whereby a closed-loop process for an optimization of an accuracy in a diagnosis of the subject provided by the neural recording method.

9. The method of claim 1, further comprising wherein a confirmation that at least one electrode is placed in the STN in step (A) is determined by an increased background activity of an electrical signal originating from the electrode, a frequent bursting of single units, an audible beta oscillation and/or somatotopic correspondence of activity with passive limb movements, or a combination thereof.

\* \* \* \* \*